United States Patent
Meulmester et al.

(10) Patent No.: US 9,966,657 B2
(45) Date of Patent: May 8, 2018

(54) INVERTED E ANTENNA WITH PARALLEL PLATE CAPACITOR FORMED ALONG AN ARM OF THE ANTENNA FOR USE WITH AN IMPLANTABLE MEDICAL DEVICE

(71) Applicant: PACESETTER, INC., Sylmar, CA (US)

(72) Inventors: Micah Meulmester, Santa Monica, CA (US); Reza Imani, Moorpark, CA (US); Wisit Lim, Santa Clarita, CA (US); Perry Li, Temple City, CA (US)

(73) Assignee: Pacesetter, Inc., Sylmar, CA (US)

(*) Notice: Subject to any disclaimer, the term of this patent is extended or adjusted under 35 U.S.C. 154(b) by 29 days.

(21) Appl. No.: 15/172,957

(22) Filed: Jun. 3, 2016

(65) Prior Publication Data
US 2016/0285158 A1    Sep. 29, 2016

Related U.S. Application Data

(63) Continuation of application No. 13/855,612, filed on Apr. 2, 2013, now Pat. No. 9,634,381, which is a
(Continued)

(51) Int. Cl.
| | |
|---|---|
| *H01Q 1/27* | (2006.01) |
| *H01Q 1/36* | (2006.01) |
| *H01Q 1/22* | (2006.01) |
| *H01Q 9/42* | (2006.01) |
| *A61N 1/372* | (2006.01) |
| *A61N 1/375* | (2006.01) |
| *A61N 1/365* | (2006.01) |
| *A61N 1/39* | (2006.01) |
| *B29C 65/48* | (2006.01) |

(Continued)

(52) U.S. Cl.
CPC ......... *H01Q 1/273* (2013.01); *A61N 1/36521* (2013.01); *A61N 1/36542* (2013.01); *A61N 1/375* (2013.01); *A61N 1/3754* (2013.01); *A61N 1/37264* (2013.01); *A61N 1/39* (2013.01); *A61N 1/3962* (2013.01); *B29C 65/48* (2013.01); *H01Q 1/22* (2013.01); *H01Q 1/36* (2013.01); *H01Q 9/0421* (2013.01); *H01Q 9/42* (2013.01); *B29L 2031/753* (2013.01)

(58) Field of Classification Search
CPC .............................. H01Q 1/273; B29C 65/48
See application file for complete search history.

(56) References Cited

U.S. PATENT DOCUMENTS 7,467,014 B2 * 12/2008 Fuller ............... A61N 1/37229
                                                        607/36
7,844,341 B2 * 11/2010 Von Arx ............. A61B 5/0031
                                                        607/60

(Continued)

*Primary Examiner* — Daniel H Lee

(57) ABSTRACT

The device includes radio frequency (RF) communication components installed within a case of the device and an antenna with an inverted E shape mounted within a header of the device. The antenna has three branches extending from a main arm: a capacitive branch connecting one end of the main arm to the case; an RF signal feed branch connecting a middle portion of the main arm to the internal RF components of the device via a feedthrough; and an inductive branch connecting the opposing (far) end of the main arm to the case to provide a shunt to ground.

13 Claims, 20 Drawing Sheets

Related U.S. Application Data continuation-in-part of application No. 13/538,501, filed on Jun. 29, 2012, now Pat. No. 9,048,541.

(60) Provisional application No. 61/793,875, filed on Mar. 15, 2013.

(51) Int. Cl.
*H01Q 9/04* (2006.01)
*B29L 31/00* (2006.01)

(56) References Cited

U.S. PATENT DOCUMENTS 7,903,043 B2 * 3/2011 Rawat ................ A61N 1/37229
　　　　　　　　　　　　　　　　　　　　343/873
8,588,924 B2 * 11/2013 Dion .................. A61N 1/37229
　　　　　　　　　　　　　　　　　　　　343/718

* cited by examiner

INVERTED E ANTENNA WITH PARALLEL PLATE CAPACITOR FORMED ALONG AN ARM OF THE ANTENNA FOR USE WITH AN IMPLANTABLE MEDICAL DEVICE

CROSS-REFERENCE TO RELATED APPLICATIONS

This application is a continuation of co-pending U.S. patent application Ser. No. 13/855,612, filed Apr. 2, 2013, which is a continuation-in-part of U.S. patent application Ser. No. 13/538,501 (issued as U.S. Pat. No. 9,048,541) of Li et al., filed Jun. 29, 2012, entitled "Inverted E Antenna with Capacitance Loading for Use with an Implantable Medical Device", and also claims priority via U.S. Provisional Patent Application No. 61/793,875 of Meulmester et al., entitled "Inverted E Antenna with Parallel Plate Capacitor Formed Along an Arm of the Antenna for Use with an Implantable Medical Device," filed Mar. 15, 2013, all of these applications are incorporated by reference herein.

FIELD OF THE INVENTION

The invention generally relates to implantable medical devices, such as pacemakers and implantable cardioverter/defibrillators (ICDs) and in particular to antennas for use therein.

BACKGROUND OF THE INVENTION

State-of-the-art pacemakers, ICDs and other cardiac rhythm management devices (CRMDs) can be equipped with radio-frequency (RF) communication devices for communicating with external systems such as bedside monitors or external diagnostics systems. In particular, RF communication devices have been developed to utilize Medical Implant Communication Service (MICS)-band radio transmissions or Medical Device Radiocommunications Service (MedRadio)-band transmissions. (MedRadio maintains the spectrum previously allocated for MICS (402-405 MHz) while adding additional adjacent spectrum (401-402 MHz and 405-406 MHz).) Herein, the term "MICS/MedRadio" will be used for the sake of completeness and generality to refer to MICS, MedRadio or both.) RF capable devices use an antenna within the header or adjacent header for receiving or transmitting RF signals. However, problems arise in designing such antennas due to the increasing miniaturization of CRMDs and their components.

In particular, there can be a loss of RF communication performance due to the reduction in size of the header and the device case (also called the housing or the "can") of the CRMD. As technology improves, the sizes of the implantable devices continue to shrink but the laws of physics regarding RF communications do not change. Since about 2005, at least some CRMD designers have employed a shorted loop antenna for RF communications. However, RF computer simulations indicate that a further reduction in device size would diminish antenna performance below acceptable levels. Accordingly, there is a need to provide improved antenna designs for use with CRMDs, especially relatively small devices.

In this regard, there are many challenges to designing a well performing antenna for use within an implantable medical device. One issue is the significant amount of attenuation inherent to the system since the RF signal travels through the lossy human body. Another problem is that the size of the antenna is limited by the size of the header (at least for devices where the antenna is to be fitted inside the header.) Ideally, the antenna should have a length equal to a quarter wave length of the operating frequency (which is typically near 400 MHz), but it is difficult to design an antenna that fits within a device header while achieving that length. Hence, for antennas to be housed in the device header, the quarter wavelength constraint can result in an antenna much smaller than needed for optimum performance. Another issue is that the antenna should have an input impedance that is the complex conjugate of impedance of the internal circuitry of the device so maximum power transfer can take place. If the impedance of the antenna is too low or too high, additional mismatch losses will occur, which will decrease signal power.

FIG. 1 illustrates an antenna 2 that attempts to meet these requirements using a folded monopole design commonly known as an "Inverted L antenna" for use within the header 4 of an exemplary CRMD 6. The Inverted L is a monopole that ideally should be sized to a quarter wavelength of its operating frequency with a 90-degree bend to resemble a downward facing L. The antenna can fit within a fairly small header volume but suffers from very low input impedance. Also, this antenna is best suited for higher gigahertz (GHz) frequency applications where the necessary antenna length for resonance is relatively short. At 400 MHz, implementing an Inverted L antenna becomes impractical for implantable device purposes, as this would require a very long antenna that would not fit within the header. To solve the impedance issue, an extra branch 7 can be connected to the Inverted L and shunted to ground. This topology, shown in FIG. 2, is known as the "Inverted F antenna." (An Inverted F antenna design is discussed, for example, in U.S. Pat. No. 7,047,076 to Li et al., entitled "Inverted-F Antenna Configuration for an Implantable Medical Device.") The extra shunt connection provides a larger input impedance for matching purposes but the Inverted F still suffers from lack of adequate length for practical applications wherein the antenna must fit within the header of a relatively small CRMD.

The parent application cited above (entitled "Inverted E Antenna with Capacitance Loading for use with an Implantable Medical Device") presented an improved antenna, particularly for MICS/MedRadio applications, that addressed these and other issues of predecessor designs. Briefly, the application described, inter alia, an antenna with an inverted E shape for mounting within the header of an implantable medical device. The antenna has three branches extending from a main horizontal arm: a capacitive branch connecting one end of the main arm to the case via a capacitive load; an RF signal feed branch connecting a middle portion of the main arm to the internal RF components of the device via a feedthrough; and an inductive branch connecting the opposing (far) end of the main arm to the case to provide a shunt to ground. The E-shaped configuration and the provision of capacitive loading allows for cancellation of inductance to bring the antenna into resonance and to provide optimal radiation efficiency as well as to provide for impedance with no reactive component. In one particular example, capacitive loading was achieved by installing a discrete capacitor along one of the branches of the antenna. In another example, the branch instead ended in a flat plate mounted via an epoxy dielectric to the case of the device so that the plate, the epoxy and the adjacent portion of the case collectively formed a parallel plate capacitor. During device design, capacitance could be set by selecting the size of the plate, the distance from the plate to the case and the electrical characteristics of the dielectric.

Although the inverted E antenna of the parent application has many advantages over predecessor designs, further room for improvement remains. For example, the use of a discrete capacitor adds to the cost of the device, particularly when a bio-compatible epoxy is required. The use of a flat plate at the end of one of the branches to provide capacitance (in conjunction with the adjacent portion of the case) requires high precision tooling to maintain the spacing between plate and the device "can" in order to produce the correct capacitance and achieve the desired RF performance. Proper spacing between the plate and the device housing can be difficult to achieve with a pre-cast header because there is considerable variance/tolerance in each individual header and also variance/tolerance in the attachment of the header to the can. Still further, the header epoxy used as the dielectric material can have inconsistencies. For example, the epoxy can develop bubbles during manufacture and can saturate with bodily fluid (saline) over time. Moreover, the header itself may shrink or warp, which can change the capacitance value created by the epoxy between the can and the plate. As a result the capacitance value may not be stable as desired over time. Still further, the plate needs to be fairly large to create an appropriate capacitance value (given the typical requirement for approximately 0.038" of spacing between the can and the plate.) The reason for this spacing is that clearance is needed to attach (i.e. backfill) the header to the housing with epoxy. A smaller gap would reduce the size of the plate but then it could be difficult for epoxy to flow consistently between the header and the can, which presents a manufacturability issue. Also, epoxy can be a relatively poor dielectric for a capacitor because it has a low dielectric constant, such that the plate size has to be larger for a given capacitance.

Accordingly, it would be desirable to provide improvements to the inverted E antenna design and it is to this end that aspects of the present invention are generally directed.

SUMMARY

In accordance with an exemplary embodiment of the invention, an implantable medical device is provided for implant within a patient wherein the device includes RF communication components installed within a case of the device for use with an antenna having an inverted E shape mounted within a header of the device. A first branch of the antenna includes a capacitor formed of a set of conducting plates with a non-conductive medium interposed between the plates. Hence, rather than generating capacitance between the device housing and a plate and the end of a branch of the antenna, a capacitor is instead formed or "embedded" along the branch itself, allowing for ease of manufacture as well as overcoming other design issues discussed above. Various advantages of exemplary embodiments of the antenna are described in detail below.

In an illustrative embodiment, the inverted E antenna is installed within a header mounted to an exterior of the case of the implantable device. The case provides a ground plane for the antenna. The antenna has three branches extending from a main horizontal arm that forms the base of the inverted "E." The three branches include: the aforementioned first branch (or "capacitive branch") connecting one end of the main arm to the case and providing an embedded capacitive load; a second "RF signal feed branch" connecting a middle portion of the main arm to the internal RF components of the device via a feedthrough (or feedthru) in the case; and a third "inductive branch" connecting the other end of the main arm to the case to provide a shunt to ground.

Note that, at MICS frequencies, a shunt (depending on its dimensions) may behave like a small inductor and hence the third branch that is shunted to ground is referred to as the inductive branch. At resonance, the capacitive loading of the first branch cancels the inductance of the third branch to provide optimal radiation efficiency as well as to provide a real impedance with substantially no reactive (i.e. Imaginary) component.

In one particular example, the capacitive branch of the antenna includes a capacitor formed of a single pair of parallel titanium plates, although additional plates may be provided. The nonconductive material provided between the plates is a dielectric such as a ceramic bonded to the plates using an epoxy. Alternatively, titanium may be sputtered onto both sides of a ceramic plate, cut to size, and then welded between the parallel plates. During device design, the amount of capacitance can be set by selecting the sizes of the plates, the distance between the plates, and the electrical characteristics of the nonconductive material between the plates. In this manner, the value of the capacitor can be selected in conjunction with other antenna design parameters to substantially cancel any inductance provided by the antenna or to achieve other goals. In particular, by properly selecting the capacitance, the resonant frequency of the antenna can be set to the operating frequency of the device to provide both very good impedance and very good performance without having to change the length or height of the antenna. The antenna may be, for example, part of a pre-cast header, which is then welded to the device housing during header attachment. In other examples, the capacitor employs multiple plates stacked in parallel to provide additional capacitance.

As with the predecessor inverted E design, the new inverted E antenna allows the impedance and resonance frequency of the antenna to be set during design to preferred or optimal values by selecting the capacitance provided by the first branch, the inductance provided by the third branch and the location of the middle RF signal feed branch relative to the first and third branches. Indeed, any change to the length and cross-sectional area of the antenna can be seen as a change in inductance, which can be canceled out with a corresponding change in the capacitor. Thus, if the latest model of the implantable device is made smaller (requiring a smaller antenna), suitable adjustments to the design of the inverted E type antenna can be made to maintain preferred or optimal impedance values. That is, the impedance can be tuned to match device circuitry. In some examples, the antenna is configured to provide an impedance of about 50 ohms with substantially no reactive components. Hence, the inverted E-shaped antenna and its components allow for great flexibility during device design to achieve operational or performance goals. Also, by allowing for a generally smaller antenna than non-inverted E designs, the header can be made smaller, thus making the overall device smaller and lighter. The antenna may be used either for transmitting or for receiving RF signals. That is, by virtue of the reciprocity theorem, the antenna is equally effective at receiving and transmitting signals. Implantable devices incorporating the antenna may be implemented using a bi-directional half duplex protocol to accommodate both reception and transmission.

BRIEF DESCRIPTION OF THE DRAWINGS

The above and further features, advantages and benefits of the invention will be apparent upon consideration of the present description taken in conjunction with the accompanying drawings, in which:

FIG. 14 provides still another view of the antenna of FIG. 12;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
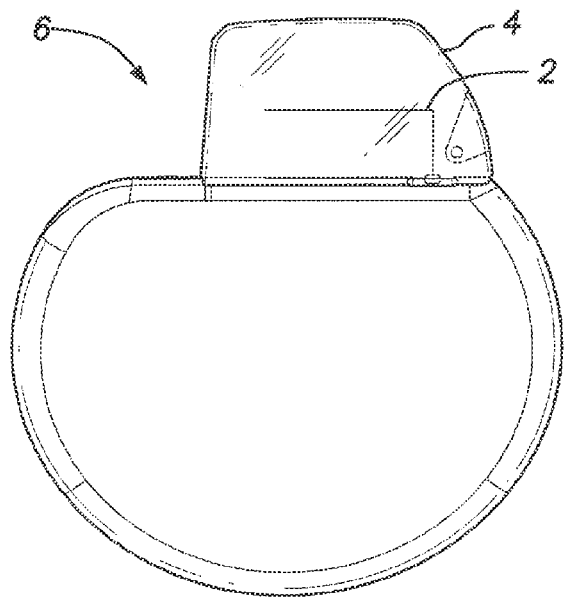
FIG. 1 illustrates a conventional inverted L antenna mounted within the header of an implantable medical device.
Figure 2:
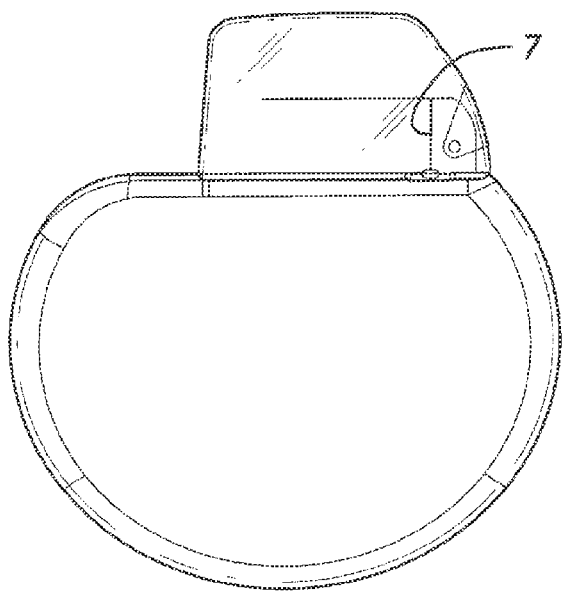
FIG. 2 illustrates a conventional inverted F antenna mounted within the header of an implantable medical device.
Figure 3:
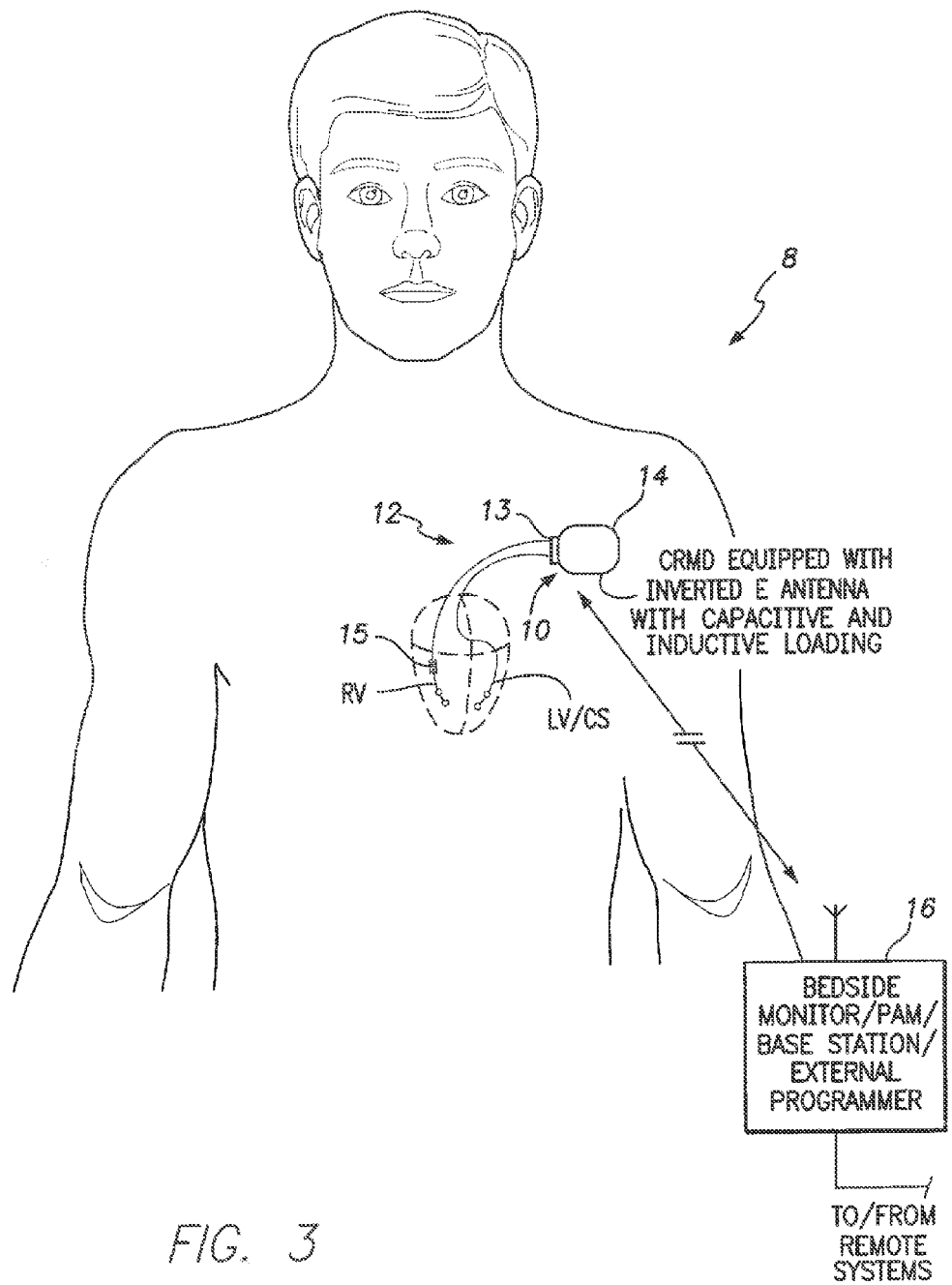
FIG. 3 illustrates pertinent components of an implantable medical system having an CRMD equipped for MICS/MedRadio communication and incorporating an inverted E antenna (mounted within a header of the device) that includes capacitive and inductive loading.
Figure 10:
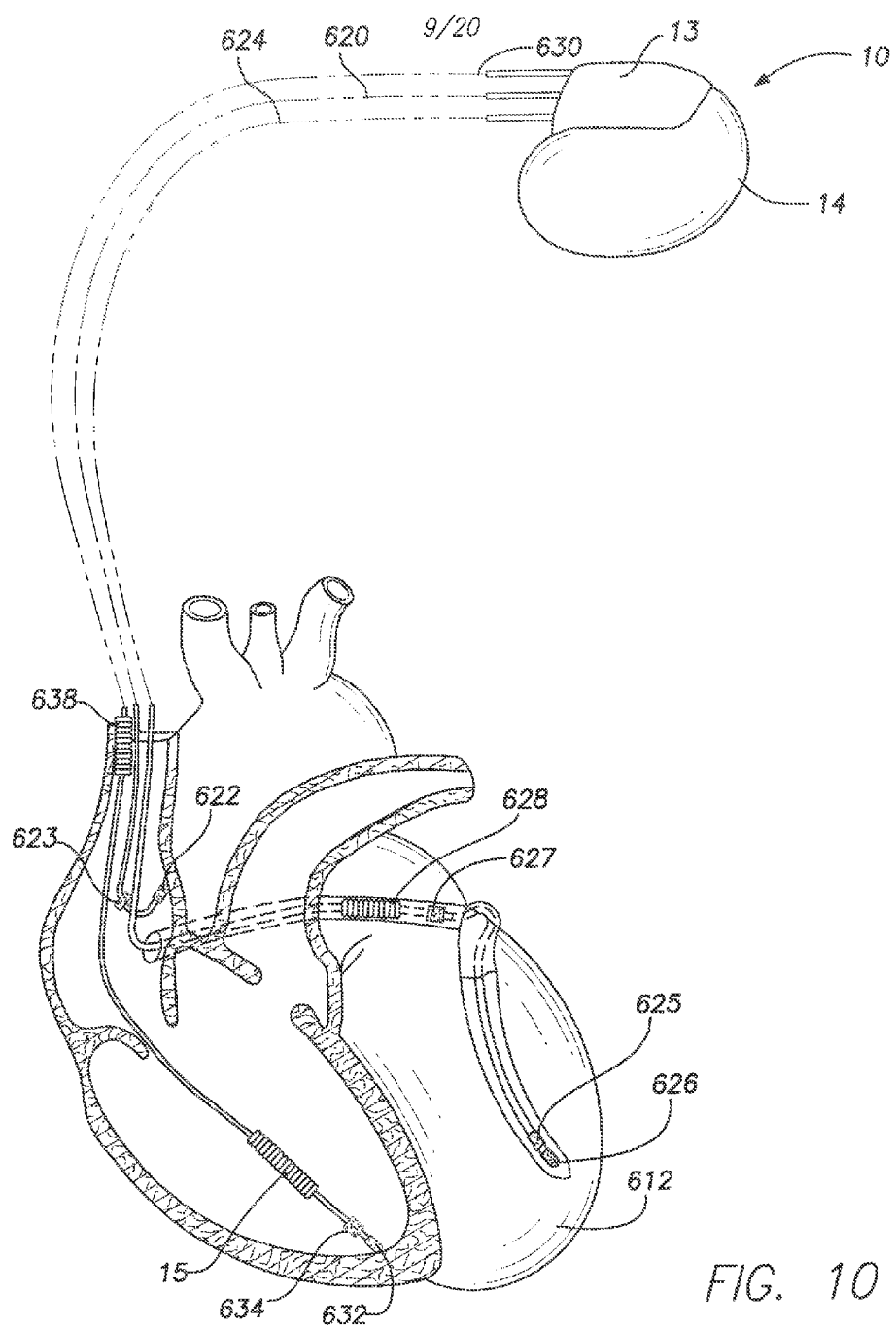
FIG. 10 is a simplified, partly cutaway view, illustrating the CRMD of FIG. 3 along with a set of leads implanted on or in the heart of the patient.

FIG. 3 illustrates an implantable medical system 8 having a CRMD 10 equipped with an inverted E antenna (not specifically shown in FIG. 3 but shown in FIGS. 4-8) for use with MICS/MedRadio transmissions and further equipped with one or more cardiac sensing, pacing and/or shocking leads 12 implanted within the heart of the patient. In some examples, the CRMD may be equipped to perform both pacing and shocking functions and may be referred to as a hybrid pacemaker/ICD or just a "hybrid." In FIG. 3, two exemplary leads are illustrated: a bipolar RV lead and a bipolar left ventricular (LV) lead implanted via the coronary sinus (CS). An RA lead may also provided that includes a bipolar RA tip/ring pair. Other suitable leads may instead be employed, including leads with more or fewer electrodes such as quadripolar leads. Also, as shown, the exemplary RV lead has an RV coil 15 implanted within the RV for delivery of defibrillation shocks (for examples wherein the CRMD is equipped to operate as an ICD.) Other electrodes of various sizes and shapes may be additionally or alternatively provided, such as an LV coil. A more complete set of leads is illustrated in FIG. 10. The inverted E antenna is installed with a header 13 mounted to an end of the case 14 (also referred to as the housing or can) of the CRMD. The header also provides connection terminals for leads 12.

MICS/MedRadio components within CRMD 10 use the inverted E antenna for communicating with an external system 16 via RF signals. External system 16 may include, for example, an external programmer, bedside monitor, base station or hand-held personal advisory module (PAM). The MICS/MedRadio components may exploit InvisiLink™ Wireless Telemetry of St. Jude Medical. For example, periodic transfers for diagnostics data may be transmitted from the CRMD to a bedside monitor located within about two meters of the patient. Data from the external system can then be forwarded to a centralized system such as the Merlin.Net system, the HouseCall™ remote monitoring system or the Merlin@home systems of St. Jude Medical so as to relay the information to a clinician.

Note that CRMD 10 can be any suitably-equipped device such as a standalone pacemaker, ICD or cardiac resynchronization therapy (CRT) device, including CRT-D and CRT-P devices) or combinations thereof. CRMDs are generally discussed, for example, in U.S. Pat. No. 5,720,767 to Amely-Velez, entitled "Impedance Dependent Implantable Cardioverter-Defibrillator." Moreover, although identified in FIG. 3 as a CRMD, it should be understood that device 10 can comprise other implantable medical devices such as neural stimulation devices or the like. The aforementioned inverted E antenna is particularly useful for MICS and/or MedRadio communications but may be useful for other purposes as well. Furthermore, it should be understood that the particular shape, size and locations of the implanted components shown in FIG. 3 are merely illustrative and may not necessarily correspond to actual implant locations. In particular, preferred implant locations for the leads are more precisely illustrated in FIG. 10.

Inverted E Antenna

Figure 4:
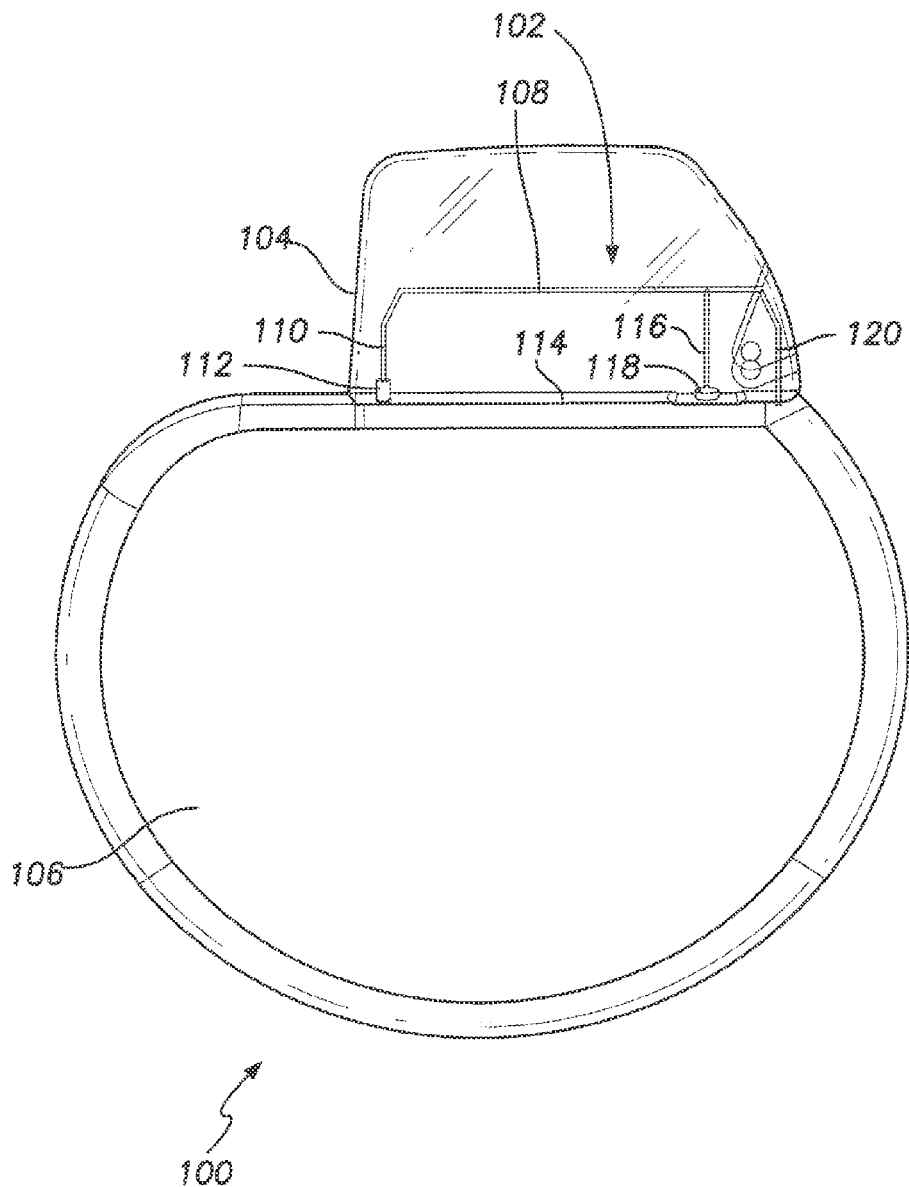
FIG. 4 illustrates the inverted E antenna of the CRMD of FIG. 3 mounted within the header of an implantable medical device.

FIGS. 4-8 illustrate various examples of the inverted E antenna, which is mounted within the header of the device. Referring next to FIG. 4, CRMD 100 includes an inverted E antenna 102 installed within header 104 mounted to the case (or housing or can) 106 of the device. The case provides a ground plane for the device. In the figure, the header is transparent simply to permit illustration of the antenna. The antenna includes a conducting main arm 108 that provides the "backbone" for the antenna. Three conducting branches extend from main arm 108 for connecting to the case or its internal components. In particular, a capacitive branch 110 extends from a first end of the main arm and includes a capacitor 112 mounted along a distal end of the branch, which is in turn electrically coupled to a conducting surface 114 inside the header. An RF signal feed branch 116 extends from a middle or central portion of the main arm and is electrically coupled to internal RF components of the device via a feedthrough 118. An inductive branch 120 extends from a second end of the main arm and is directly connected to conducting surface 114 to provide a shunt to ground. Branch 120 is referred to herein as an inductive branch since its length can be adjusted during antenna design to vary the inductance of the antenna to help achieve a desired impedance. In other examples, an actual inductor might be mounted to branch 120 (or elsewhere on the antenna) to provide additional impedance, if desired.

Note that due to the nature of how this antenna works, the RF feed should be the middle branch in the E structure. However, the RF signal feed branch need not be connected at the center of the main arm and, as shown, can be mounted closer to one end or the other, as appropriate. The electrical characteristics of the antenna can be adjusted, in part, based on the relative location of the middle branch along the main arm. In the particular example of FIG. 4, the RF signal feed branch is mounted closer to the inductive branch than the capacitive branch. The positions and lengths of the shunt and capacitive branches will depend upon the form factor of the header and what is required for optimum performance. Although not shown in FIG. 4, additional components may be mounted within the header, such as mounting devices (discussed below) for connecting to the proximal ends of pacing or sensing leads. Note also that the wire antenna itself can have a rectangular or circular cross section depending on what is preferable to meet size and performance requirements.

Figure 5:
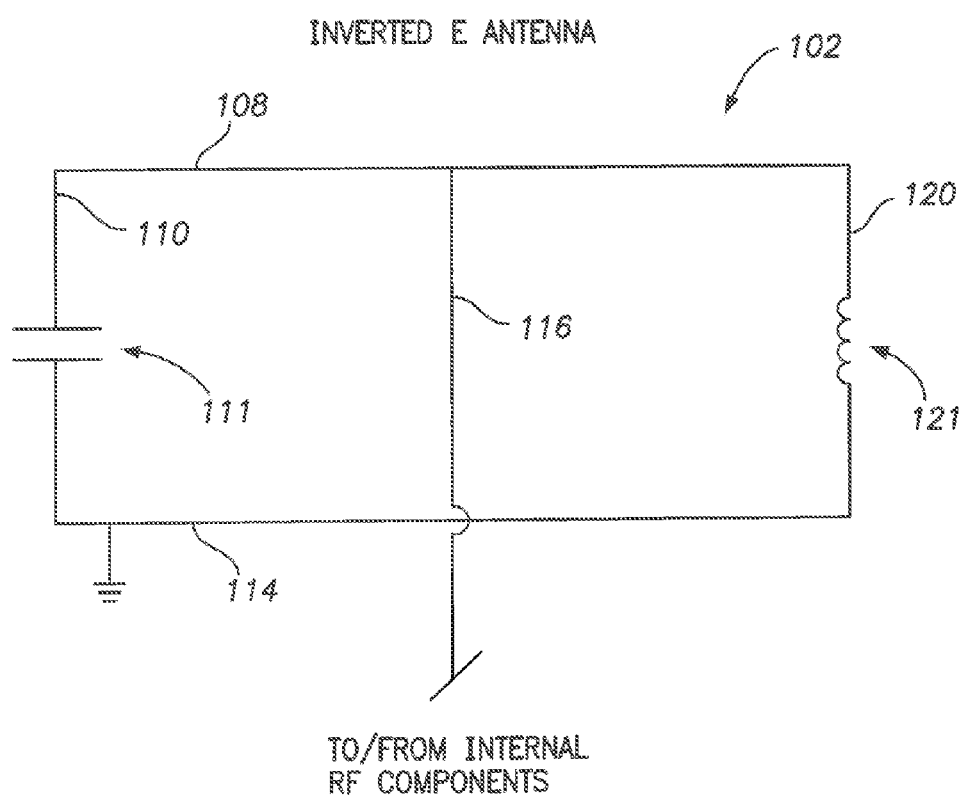
FIG. 5 is a schematic of the inverted E antenna of FIG. 4.

FIG. 5 provides a schematic illustration of the antenna circuit. Briefly, antenna 102 includes first branch 110 connected to ground 114 for providing capacitance 111, second branch 116 connected directly to internal RF components of the device for providing a signal feed, and third branch 120 connected to ground for providing inductance 121, where each of the branches is also connected as shown to main conducting arm 108. In some examples, the capacitance and inductance are set to provide an impedance of about 50 ohms with substantially no imaginary components (at least at MICS or MedRadio operating frequencies such as 400 MHz.)

Figure 6:
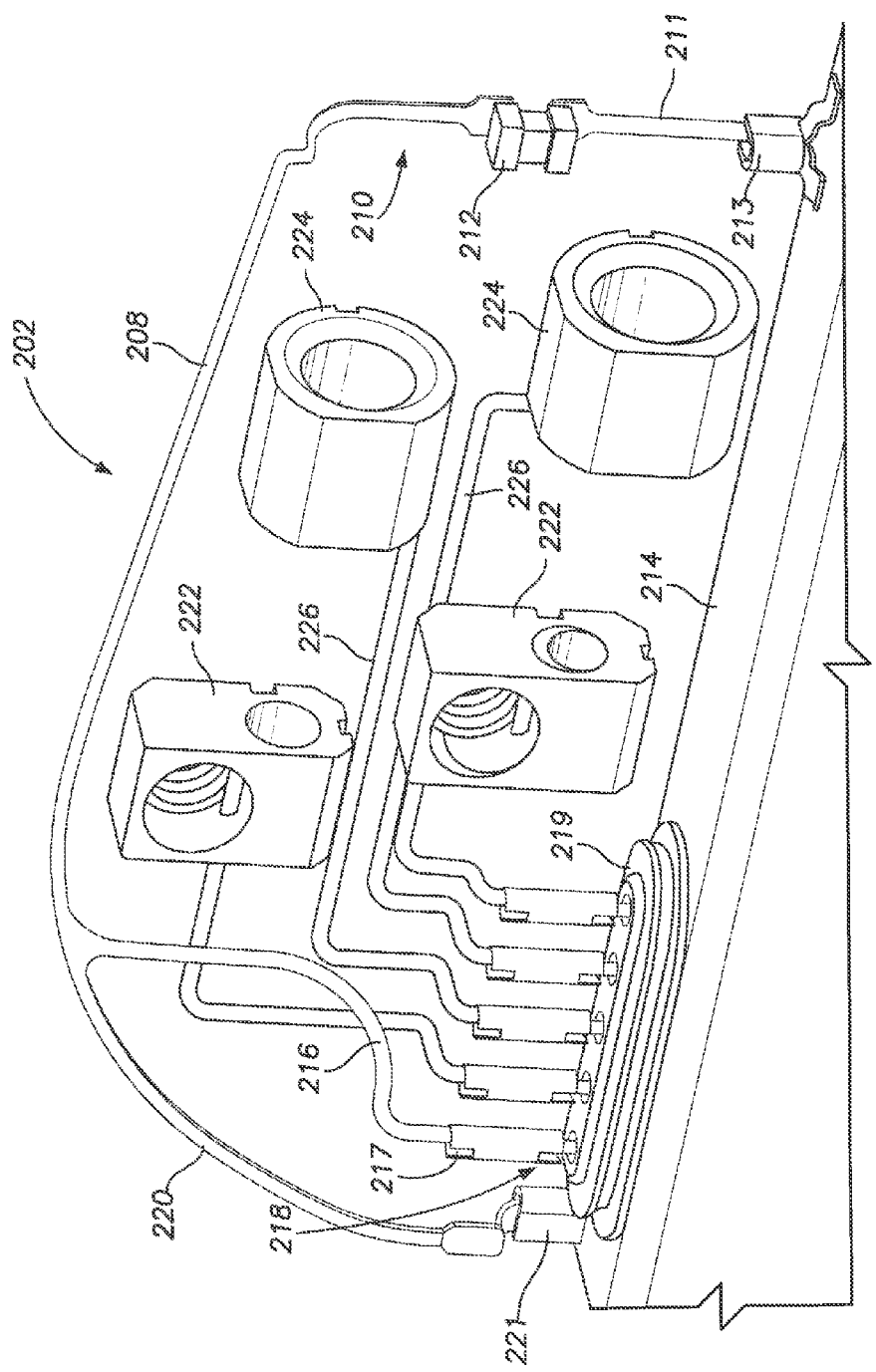
FIG. 6 illustrates an alternative embodiment of the inverted E antenna of FIG. 4 wherein the branches are curved.

FIG. 6 illustrates an exemplary inverted E antenna 202 in greater detail along with other components that may be installed within a device header for coupling to pacing, sensing and/or shocking leads. The antenna again includes a main arm 208 along with three conducting branches. A capacitive branch 210 includes a discrete surface mount technology (SMT) capacitor 212 mounted in series between arm 208 and an RF case connector 213 mounted to conducting surface 214 inside the header (where the header is not shown in this illustration.) An RF signal feed branch 216 is connected from a middle portion of arm 208 to internal RF components of the device via an RF lead connection 217 mounted to a feedthrough channel 218 of a main feedthrough assembly 219. (Feedthrough 218 can include an outer conductor which is grounded to the can, an inner conductor which is a pin running though the center of the feedthrough, and a dielectric material that separates the inner and outer conductor. Inside the can, the feedthrough pin connects to the RF circuitry and transceiver.) An inductive branch 220 extends from main arm 208 and is connected to conducting surface 214 via an RF case connector 221 to provide a shunt to ground. Additionally, FIG. 6 shows components 222 and 224 for connecting proximal ends of the aforementioned leads to internal components of the CRMD via various connection lines 226 via feedthrough assembly 219. In one example, components 222 are ring connectors for connecting to conductors within the leads that couple to ring electrodes at the distal ends of the leads. Components 224 are tip connectors for connecting to conductors of the leads that couple to tip electrodes at the distal ends of the leads.

In one particular example, the following sizes and dimensions are used: inductive branch 220, main arm 208 and the portion of capacitive branch 210 leading to capacitor 212 are referred to collectively as Antenna Part A and have an overall length of 1.8" (i.e. 1.8 inches) and a thickness of 0.10"; RF signal feed branch 216 is referred to as Antenna Part B and has a length of 0.5" and a thickness of 0.10"; capacitive branch portion 211 connecting capacitor 212 to connector 213 is referred to as Antenna Part C and has a length of 0.3" and a thickness of 0.10". Capacitor 212 has a case size designator of "0805" (with dimensions of 079" by 0.049" by 0.051") and provides a capacitance of about 2.7 picoFarads (pF.) With this overall configuration, the antenna inductance is about 58.6 nanoHenries (nH.) It should be understood that these are just exemplary values for one example. Other dimensions and components would be used with differing values for capacitance and inductance in other examples. Still further, rather than using wires to form the main arm and branches of the antenna, other conducting elements might be used, including elements incorporating conducting fluids. Preferably, the capacitor is implemented so that it can be altered if the impedance or resonance frequency of the rest of the antenna changes during device design. In the example of FIG. 6, this would be accomplished by replacing capacitor 212 with a different capacitor providing a different amount of capacitance.

Figure 7:
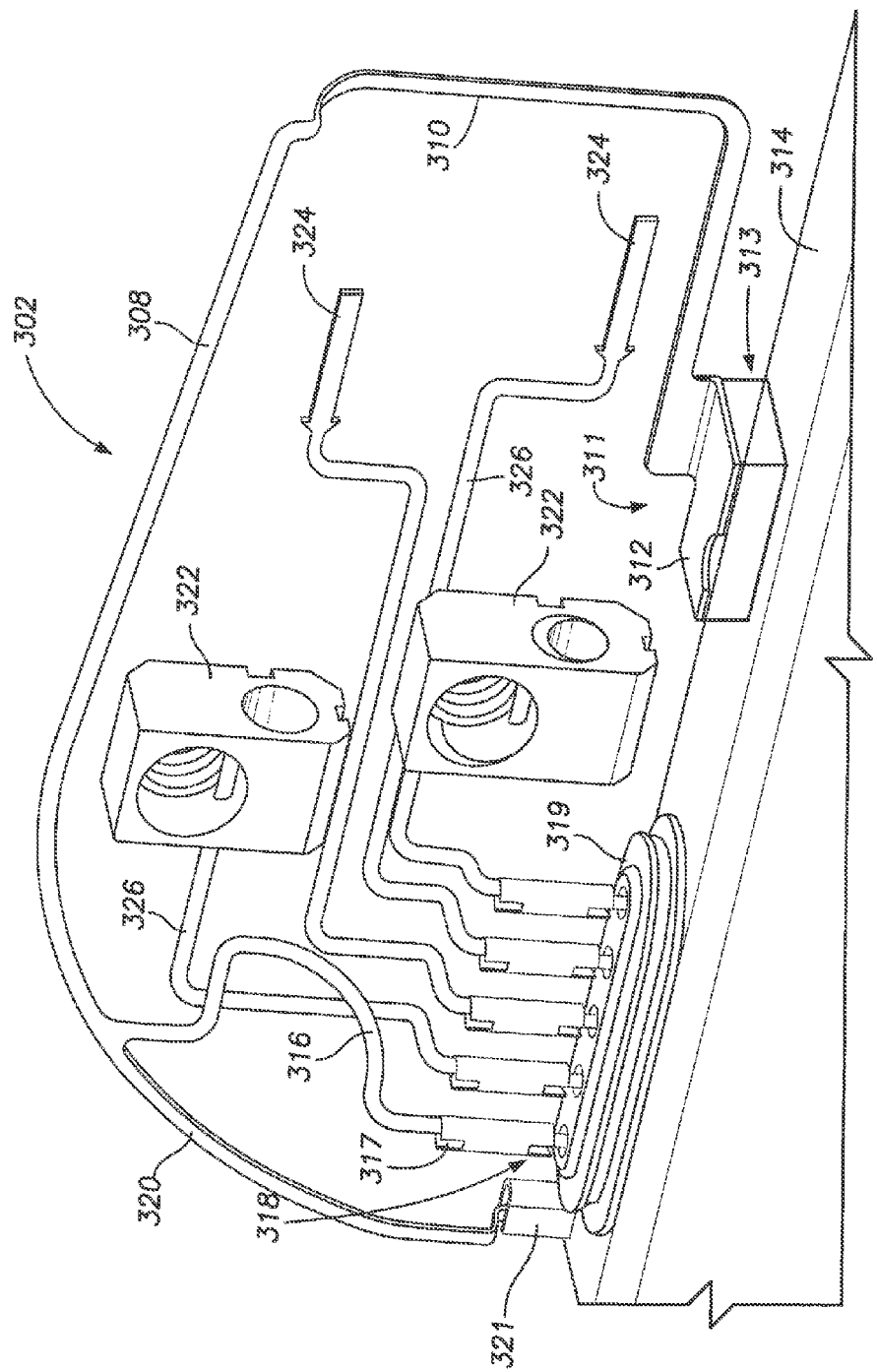
FIG. 7 illustrates another embodiment of the inverted E antenna of FIG. 4 wherein an capacitor integrated plate is employed.

FIG. 7 illustrates an exemplary inverted E antenna 302 that includes an integrated parallel plate capacitor. Many of the features of antenna 302 are the same or similar to that of antenna 202 and hence will not be described again in detail. Antenna 302 includes a main arm 308 and three branches: a capacitive branch 310; an RF signal feed branch 316 connected to internal RF components via a connector 317 mounted to feedthrough channel 318 of main feedthrough assembly 319; and an inductive branch 320 connected to surface 314 via electrical connector 321 to provide a shunt to ground. In this example, however, rather than installing a capacitor along the capacitive branch, an end of the branch provides an integrated capacitor 311. That is, a distal end of branch 310 includes a plate portion 312, which is mounted via a dielectric epoxy 313 (or another suitable plastic material) to surface 314 to provide capacitance. FIG. 7 also shows components 322 for lead connection. To more clearly show the parallel plate capacitor, FIG. 7 does not show devices corresponding to components 224 of FIG. 4 but instead just shows connection terminals 324. Note that the presence of metal devices in close proximity to the antenna (such as various tip and ring connectors) could affect the operation of the antenna and hence should be taken into account during antenna design to achieve a desired impedance and resonance frequency. This is particularly true in designs where the capacitor is not isolated from the outside environment (as in FIG. 7.) For cases where the capacitor is packaged (FIGS. 6 and 8), metal components near the antenna should have negligible impact.

In one particular example, the following sizes and dimensions are used: inductive branch 320, main arm 308 and capacitive branch 310 are referred to collectively as Antenna Part A and have an overall length of 2.2" and a thickness of 0.10"; and RF signal feed branch 316 is referred to as Antenna Part B and has a length of 0.5" and a thickness of 0.10". The epoxy used for dielectric 313 is HYSOL EE0079/HD0070 made by Loctite™ and provides a dielectric constant of about 3.8. In the example where HYSOL EE0079/HD0070 is used, plate 312 has dimensions of 0.100" by 0.260" with a plate thickness of about 0.010" and is mounted at a distance of 0.038" from surface 314 to provide a plate capacitance of about 1.3 pF. With this overall configuration, the antenna inductance is about 121 nH. Note that by varying the area of the plate and the distance between the plate and housing (as well as the type of epoxy), different capacitance values can be achieved. In particular, if the impedance or resonance frequency of the antenna changes during device design, the spacing between the plate and the case could be changed to provide a different capacitance.

Figure 8:
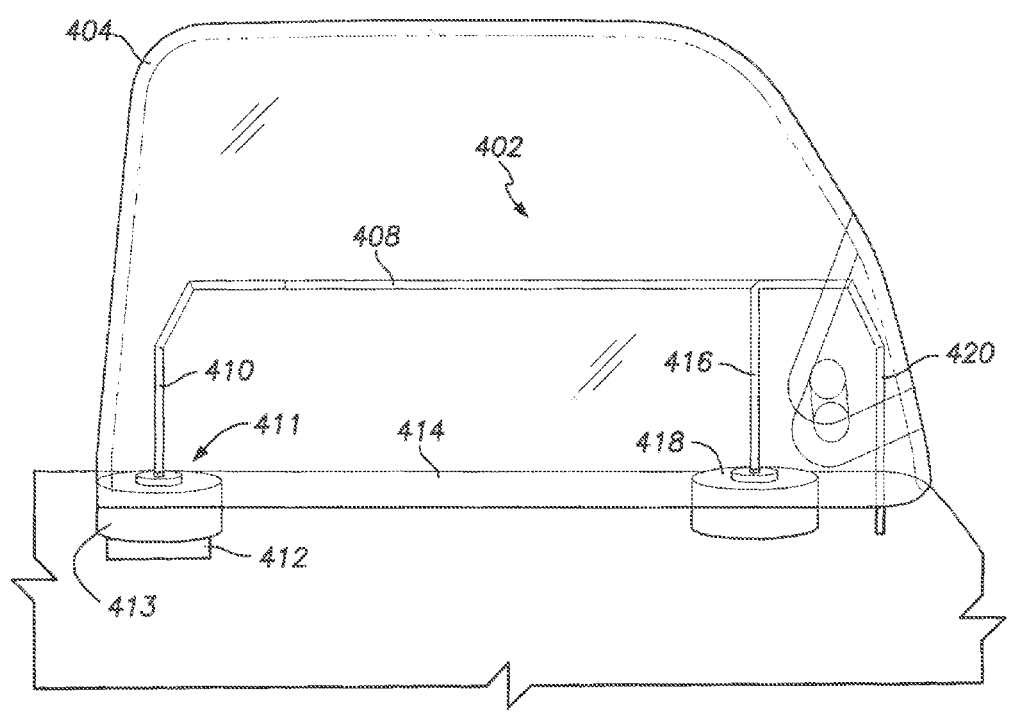
FIG. 8 illustrates yet another embodiment of the inverted E antenna of FIG. 4 wherein a discoidal capacitor is employed.

FIG. 8 illustrates an exemplary inverted E antenna 402 that includes a discoidal capacitor. Many features are the same or similar to those already described and hence will not be described again in detail. Antenna 402 is mounted within a header 404 (shown transparent to permit illustration of the antenna.) The antenna again includes a main arm 408 and three conducting branches: a capacitive branch 410; an RF signal feed branch 416 connected to internal RF components via a feedthrough 418; and an inductive branch 420 to provide a shunt to ground. In this example, however, rather than installing a capacitor along the capacitive branch inside the header, the capacitor is mounted inside the case. That is, an end of branch 410 extends through case surface 414 via a feedthrough 411 to a first terminal of a discoidal capacitor 412 (shown extending below the outer flange 413 of the feedthrough, which is mounted to an interior surface of the case. A second, opposing terminal of the capacitor is electrically connected to the interior of the case. With this configuration, although the capacitor is mounted inside the case, it is still connected in series between the main arm of the antenna and the case (which provides the ground plane for the device.) That is, the antenna functions in the same manner as shown in FIG. 5. Nevertheless, by positioning the capacitor inside the case rather than inside the header, the capacitor does not take up space within the header. In one particular example, discoidal capacitor 412 is a multi-layer ceramic capacitor providing a capacitance of 10 pF and the other antenna components are configured to yield an overall inductance of 15.8 nH.

Figure 9:
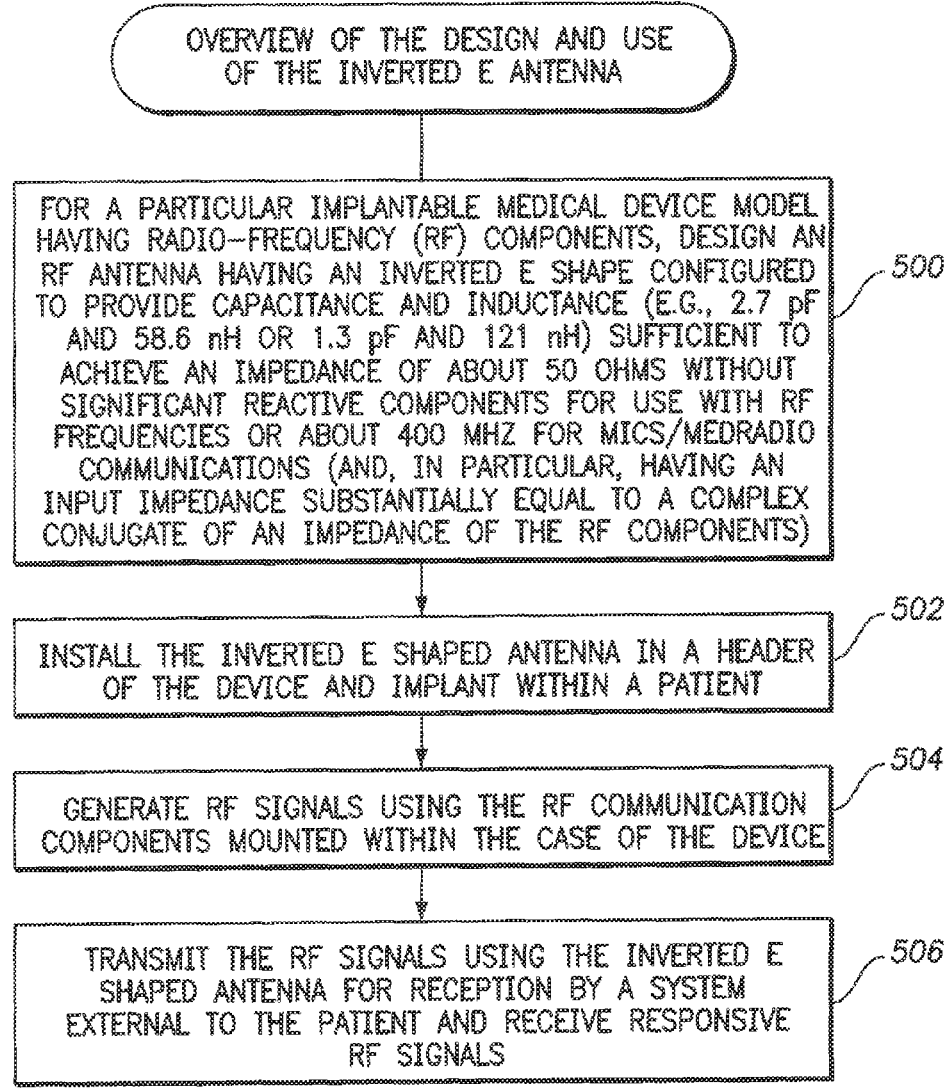
FIG. 9 illustrates exemplary techniques pertaining to designing and using the inverted E antenna of FIGS. 3-8.

FIG. 9 broadly summarizes a procedure for designing and using an inverted E antenna. Briefly, at step 500, for a particular implantable medical device model having RF components, an RF antenna having an inverted E shape is designed and configured to provide capacitance and inductance sufficient to achieve an impedance of, in one example, about 50 ohms without significant reactive components for use with RF frequencies of about 400 MHz for MICS/MedRadIo communications (and, in particular, having an input impedance substantially equal to a complex conjugate of an impedance of the RF components.) The exemplary capacitance and inductance values discussed above are listed in FIG. 9. In other examples, different values might be used to achieve a different impedance. At step 502, the inverted E shaped antenna is installed in a header of the device and implanted within a patient. At step 504, RF signals are generated using RF communication components mounted within the case of the device and, at step 506, the RF signals are transmitted using the inverted E shaped antenna for reception by a system external to the patient. Signals generated by the external system may also be received by the antenna and routed to the internal RF components of the implanted device for use in controlling the operation of the device. The broad summary of FIG. 9 does not, of course, set forth all steps that may be needed. In particular, approval by the U.S. Food and Drug Administration (FDA) or other regulatory authorities may be required before implant of the device within a patient.

Although primarily described with respect to examples wherein the implanted device is a CRMD, other implantable medical devices may be equipped to exploit the techniques described herein. Where appropriate, the antenna described herein may be used in conjunction with other antenna design features. See, for example, shielding features described in U.S. patent application Ser. No. 13/458,934 of Amely-Velez et al., filed Apr. 27, 2012, and entitled "Electromagnetic Interference Shielding for use with an Implantable Medical Device Incorporating a Radio Transceiver". Also, it should be understood that any "optimal" antenna parameters or dimensions described herein are not necessarily absolutely optimal in a mathematical sense. What constitutes "optimal" depends on the criteria used for judging the resulting performance. The antenna parameters identified or selected using techniques described herein represent, at least, a "preferred" set of parameters. Designers may choose to adjust or alter the parameters at their discretion during device design.

For the sake of completeness, an exemplary CRMD will now be described, which includes components for performing controlling pacing and shocking.

Exemplary CRMD

FIG. 10 provides a simplified block diagram of the CRMD, which in this example is a dual-chamber hybrid device capable of treating both fast and slow arrhythmias with stimulation therapy, including cardioversion, defibrillation, and pacing stimulation. (A single chamber CRMD could instead be used.) To provide atrial chamber pacing stimulation and sensing, CRMD 10 is shown in electrical communication with a heart 612 by way of a right atrial lead 620 having an atrial tip electrode 622 and an atrial ring electrode 623 implanted in the atrial appendage. CRMD 10 is also in electrical communication with the heart by way of a right ventricular lead 630 having, in this embodiment, a ventricular tip electrode 632, a right ventricular ring electrode 634, a right ventricular (RV) coil electrode 15, and a superior vena cava (SVC) coil electrode 638. Typically, the right ventricular lead 630 is transvenously inserted into the heart so as to place the RV coil electrode 15 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, CRMD 10 is coupled to a "coronary sinus" lead 624 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 9, it should also be understood that additional stimulation leads (with one or more pacing, sensing and/or shocking electrodes) might be used in order to efficiently and effectively provide pacing stimulation to the left side of the heart or atrial cardioversion and/or defibrillation. Alternatively, fewer leads or electrodes might be used. In particular, in many embodiments, no LA coil 628 is included. Note that a portion 13 of CRMD 10 represents the header of the device (to which the leads are connected.) Within the header, the aforementioned inverted E antenna is mounted.

Figure 11:
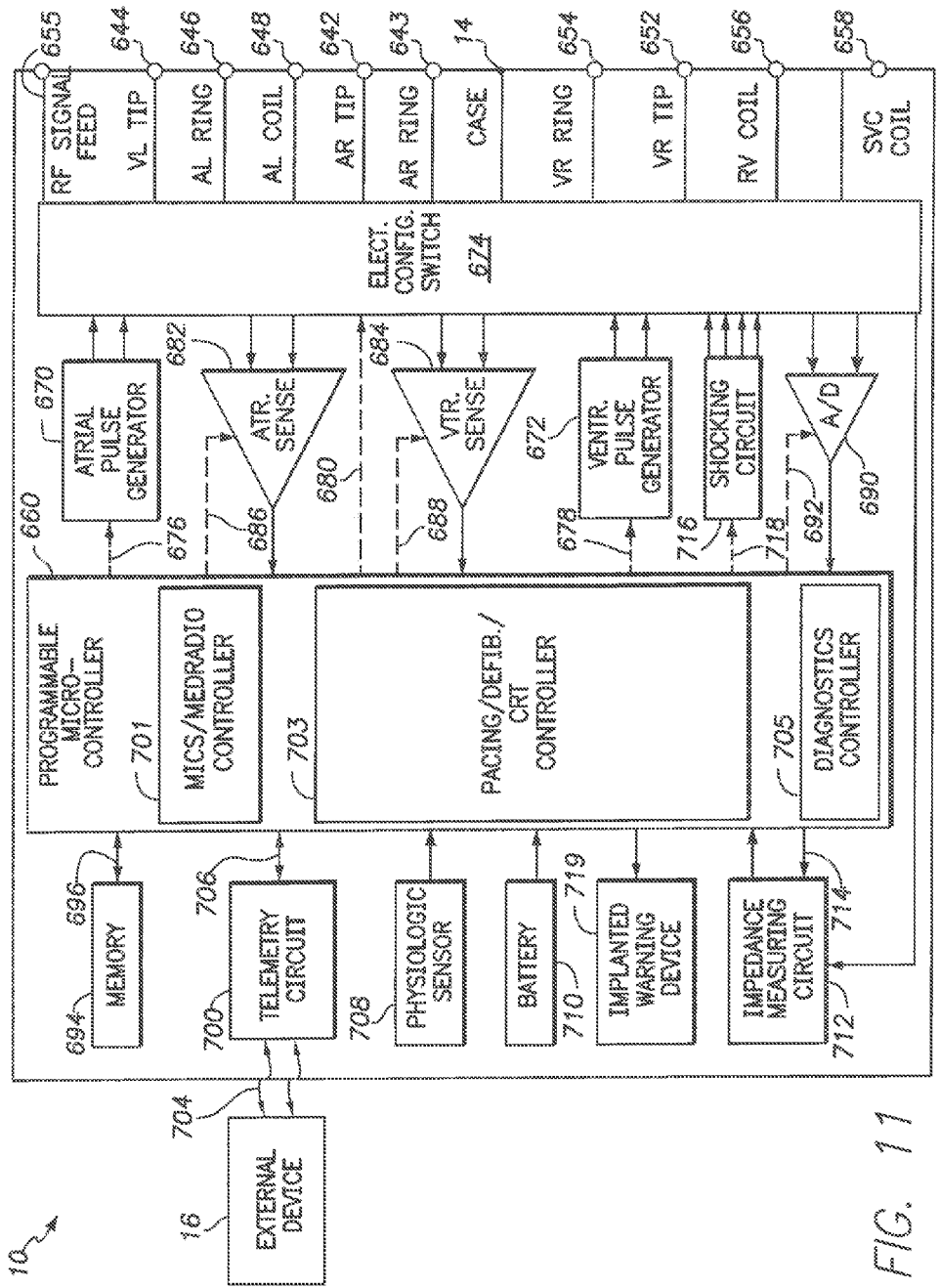
FIG. 11 is a functional block diagram of the CRMD of FIG. 10, illustrating basic circuit elements that provide cardioversion, defibrillation and/or pacing stimulation in the heart, as well as components for MICS/MedRadio communication.

A simplified block diagram of internal components of CRMD 10 is shown in FIG. 11. While a particular CRMD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 14 for CRMD 10, wherein the housing is shown schematically in FIG. 11, is often referred to as the "can", "case" or "case electrode" and may be programmably selected to act as the return electrode for all "unipolar" modes. The housing 14 may further be used as a return electrode alone or in combination with one or more of the coil electrodes, 628, 15 and 638, for shocking purposes and, as noted above, may be used as the ground plane for the antenna of the device. Note that the diagram of FIG. 11 does not illustrate the aforementioned inverted E antenna, which is illustrated within figures already described. The housing 14 includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal (Rv COIL) 656, and an SVC shocking terminal (SVC COIL) 658, which are adapted for connection to the right ventricular tip electrode 632, right ventricular ring electrode 634, the RV coil electrode 15, and the SVC coil electrode 638, respectively. Still further, RF signal feed terminal 655 is provided for connection to the RF signal feed branch of the inverted E antenna. The inductive and capacitive branches of the antenna are connected to case 14, as already explained.

At the core of CRMD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 11, an atrial pulse generator 670 and a ventricular/impedance pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables CRMD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, CRMD 10 utilizes the atrial and ventricular sensing circuits, 682 and 684, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of CRMD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRMD 10 may be non-invasively programmed into the memory 694 through a telemetry circuit 700 in telemetric communication with the external device 16, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of CRMD 10 (as contained in the microcontroller 660 or memory 694) to be sent to the external device 16 through an established communication link 704. Depending upon the implementation, the telemetry circuit may exploit MICS/MedRadio components connected to the inverted E antenna to facilitate telemetry. CRMD 10 further includes an accelerometer or other physiologic sensor 708, commonly referred to as a "rate-responsive" sensor because it is typically used to adjust pacing stimulation rate according to the exercise state of the patient. However, physiological sensor 708 may further be used to detect changes in cardiac output, changes in the physiological condition of the heart, or diurnal changes in activity (e.g., detecting sleep and wake states) and to detect arousal from sleep. Accordingly, microcontroller 660 responds by adjusting the various pacing parameters (such as rate, AV Delay, V-V Delay, etc.) at which the atrial and ventricular pulse generators, 670 and 672, generate stimulation pulses. While shown as being included within CRMD 10, it is to be understood that physiologic sensor 708 may also be external to CRMD 10 yet still be implanted within or carried by the patient. A common type of rate responsive sensor is an activity sensor incorporating an accelerometer or a piezoelectric crystal, mounted within the housing of the CRMD. Other types of physiologic sensors are known including, for example, sensors that sense the oxygen content of blood, respiration rate and/or minute ventilation, pH of blood, ventricular gradient, pulmonary artery pressure, etc.

The CRMD additionally includes a battery 710, which provides operating power to all of the circuits shown in FIG. 11. The battery 710 may vary depending on the capabilities of CRMD 10. If the system only provides low voltage therapy, a lithium iodine or lithium copper fluoride cell may be utilized. For CRMD 10, which employs shocking therapy, the battery 710 must be capable of operating at low current drains for long periods, and then be capable of providing high-current pulses (for capacitor charging) when the patient requires a shock pulse. The battery 710 must also have a predictable discharge characteristic so that elective replacement time can be detected. Accordingly, CRMD 10 is preferably capable of high voltage therapy and appropriate batteries.

As further shown in FIG. 11, CRMD 10 is shown as having an impedance measuring circuit 712, which is enabled by the microcontroller 660 via a control signal 714. The impedance circuit may be used for detecting thoracic and/or cardiogenic impedance. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; detecting the opening of heart valves. The impedance measuring circuit 712 is advantageously coupled to the switch 674 so that any desired electrode may be used.

In the case where CRMD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a high voltage shocking circuit 716 by way of a control signal 718. The shocking circuit 716 generates shocking pulses of low (up to 0.5 joules), moderate (0.5-10 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 15, and/or the SVC coil electrode 638. The housing 14 may act as an active electrode in combination with the RV electrode 15, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 6-40 joules or more), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Microcontroller 660 also includes various components directed to controlling MICS/MedRadio communication, defibrillation and diagnostics. Briefly, a MICS/MedRadio controller 701 controls MICS/MedRadio communications using the aforementioned inverted E antenna, as described above. (The inverted E antenna, which is mounted within a header of the device, is not specifically shown in FIG. 11.) A controller 703 controls delivery of pacing, defibrillation shocks, CRT or other therapies depending upon the capabilities of the device. Diagnostics pertinent to MICS/MedRadio communications, defibrillation or any other functions of the device may be generated under the control of diagnostics controller 705 for storage within memory 694 for transfer to an external device.

Depending upon the implementation, the various components of the microcontroller of the implanted device may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

In the following, additional and alternative implementations of the inverted E antenna are described. Many of the features and advantages of the antenna, and the header in which it is installed, have been described above and will not be re-described here.

Inverted E Antenna with Parallel Plates Formed Along Capacitive Branch

Figure 12:
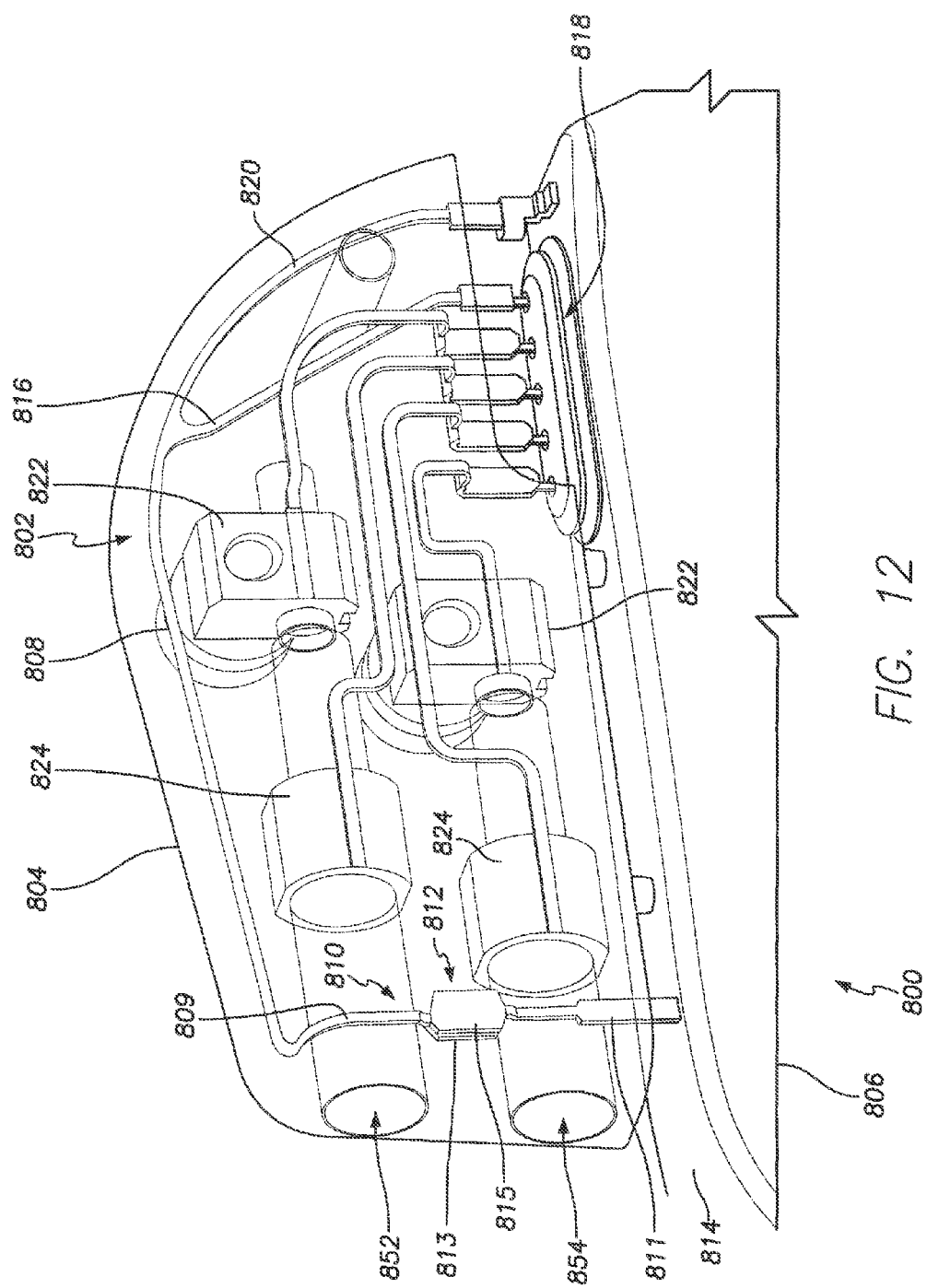
FIG. 12 illustrates another embodiment of the inverted E antenna of FIG. 3, wherein a set of conducting plates are formed along the capacitive branch for use with a dielectric material (not specifically shown in this figure)

FIGS. 12-19 illustrate various examples of the alternative embodiment of inverted E antenna, which include parallel plates formed along the capacitive branch for providing an "embedded" capacitor along the branch. Referring first to FIG. 12, CRMD 800 includes an inverted E antenna 802 installed within header 804 mounted to the case 806 of the device (wherein the header is shown as being transparent for the purposes of the drawing.) The antenna includes a main conducting arm 808 with three conducting branches extend therefrom for connecting to the case or its internal components. In particular, a capacitive branch 810 may be formed of titanium and includes a proximal portion 809 and a distal portion 811 joined by a capacitor 812. In this manner, the capacitor is formed or "embedded" within the capacitive branch between the main arm and the distal end of capacitive branch, which is electrically coupled to a conducting surface 814 of case 806 inside the header. More specifically, capacitor 812 is formed of a pair of parallel conducting plates 813 and 815, which may also be formed of titanium, with a non-conductive material (e.g. a ceramic dielectric) interposed therebetween. (Note that titanium may also be used in the antenna embodiments described above, such as in the capacitor plate of FIG. 7.) In FIG. 12 and in several of the drawings described herein below, the non-conductive material is not shown so that the shape and spacing of the plates can be more clearly seen. The non-conductive material and methods for interposing it between the plates will be discussed below with reference to FIGS. 18 and 19.

Thus, in the embodiment of FIG. 12, capacitive arm 810 consists of two portions, segments or ribbons, 809 and 811, interconnected by capacitor 812. First ribbon 809 is integral with the main arm of the antenna. Second ribbon 811 is physically separate but is coupled to the first ribbon via the non-conductive material that is interposed between the pair of parallel plates.

Collectively, first ribbon 809, second ribbon 811 and capacitor 812 comprise the "capacitive arm" of the inverted E antenna. It should be understood that additional plates might be used, rather than merely two, to form the capacitor and that, in some examples, the plates might not be flat or parallel but may instead be formed with other suitable shapes. FIG. 12 also shows other components of the header, discussed above, such as ring connectors 822 and tip connectors 824. The figure also shows various entry bores (such as 852 and 854) for insertion of sensing/pacing lead tip connectors into the aforementioned header tip connector components. As shown, the parallel plates of capacitor 812 may be formed along arm 810 for positioning the plates within the space between two of the bores. If needed, the lower of the two bores (854) may be positioned closer to the device housing to accommodate the capacitor.

As with the embodiments described above, the inverted E antenna of FIG. 12 includes an RF signal feed branch 816 that extends from a middle portion of the main arm and is electrically coupled to internal RF components of the device via a feedthrough 818. An inductive branch 820 extends from a second end of the main arm and is directly connected to conducting surface 814 of the case to provide a shunt to ground. Branch 820 is referred to as the inductive branch since (as described above) its length can be adjusted during antenna design to vary the inductance of the antenna to help achieve a desired impedance. In other examples, an actual inductor might be mounted to branch 820 (or elsewhere on the antenna) to provide additional impedance, if desired. As already explained, the inverted E antenna design allows the impedance and resonance frequency of the antenna to be set during design to preferred or optimal values by selecting the capacitance provided by the first branch, the inductance provided by the third branch and the location of the middle RF signal feed branch relative to the first and third branches. Thus, if the latest model of the implantable device is made smaller (requiring a smaller antenna), suitable adjustments to the design of the inverted E type antenna can be made to maintain preferred or optimal impedance values.

Figure 13:
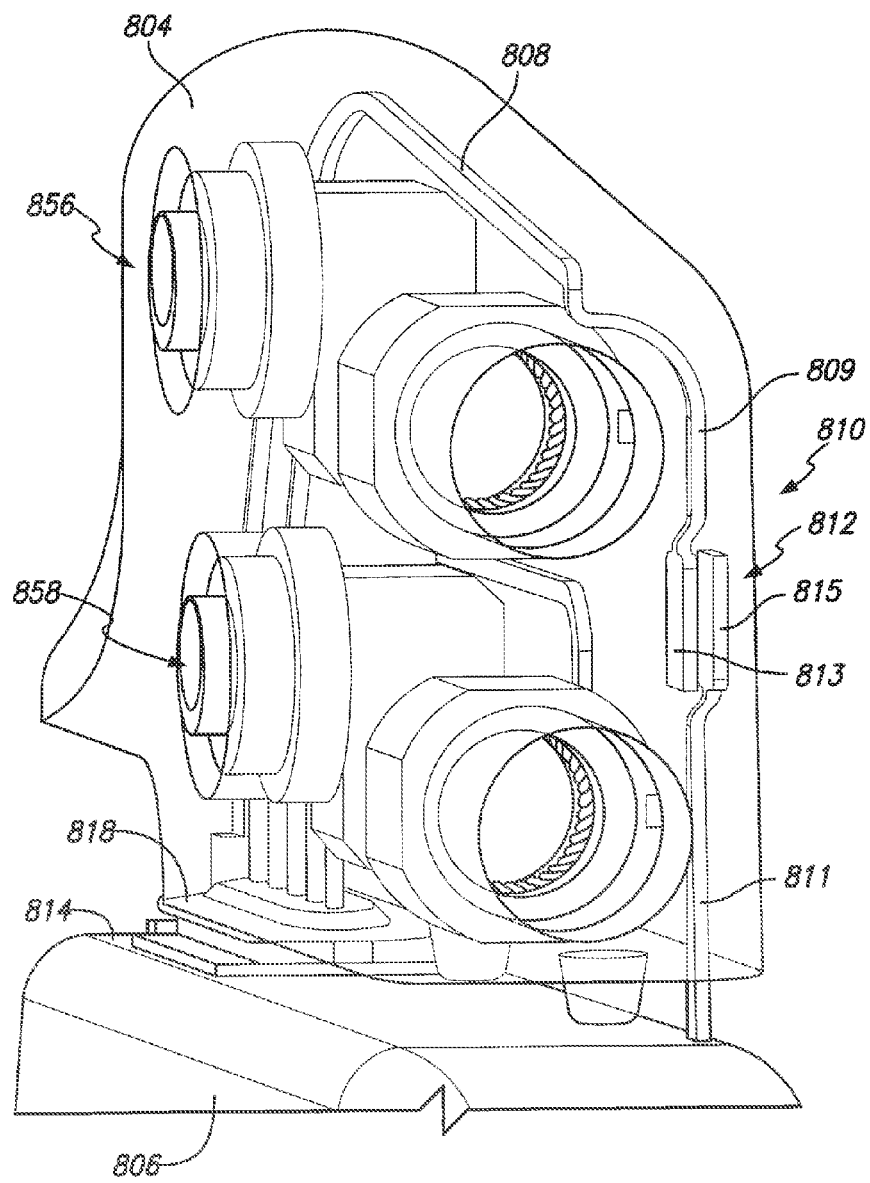
FIG. 13 provides an alternative view of the antenna of FIG. 12.
Figure 14:
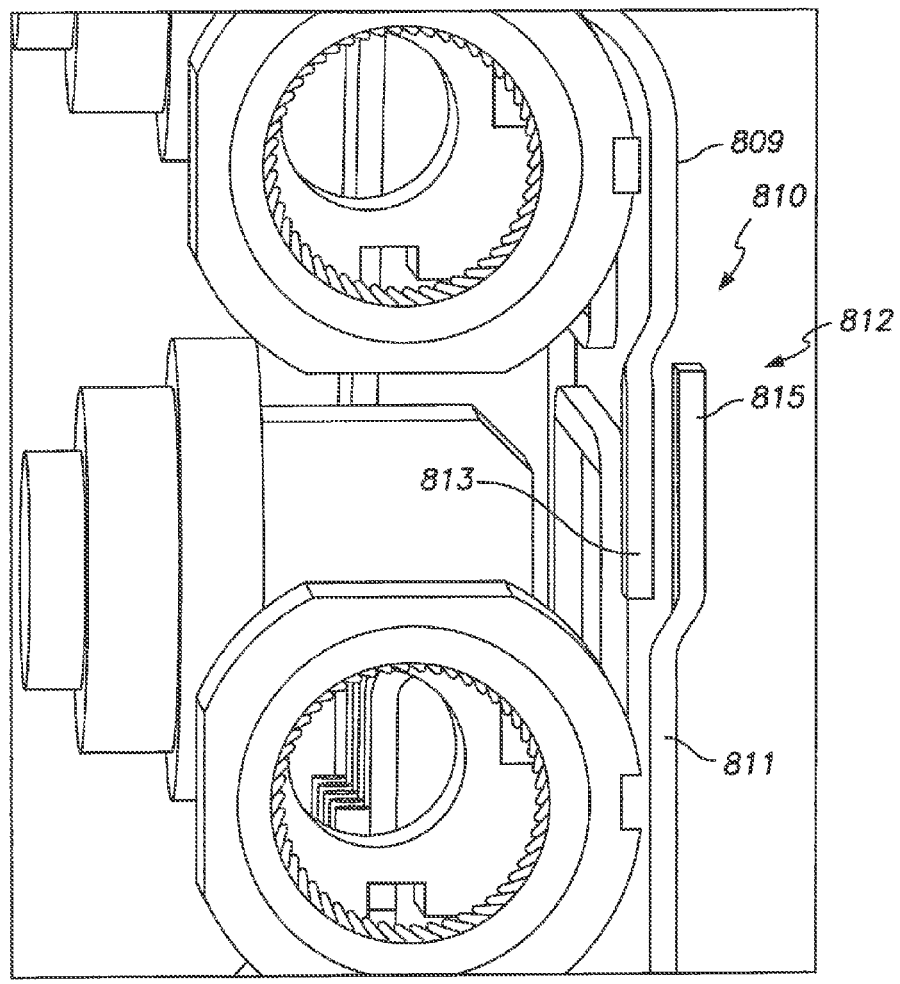
FIG. 14 provides another view of the antenna of FIG. 12.
Figure 15:
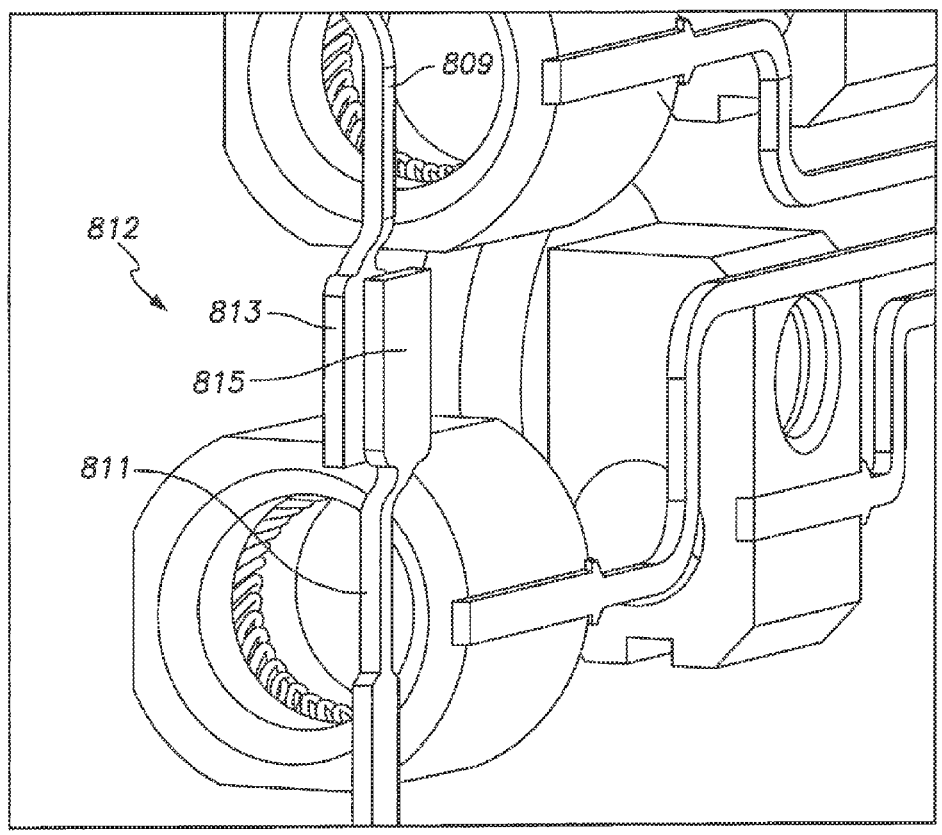
Figure 16:
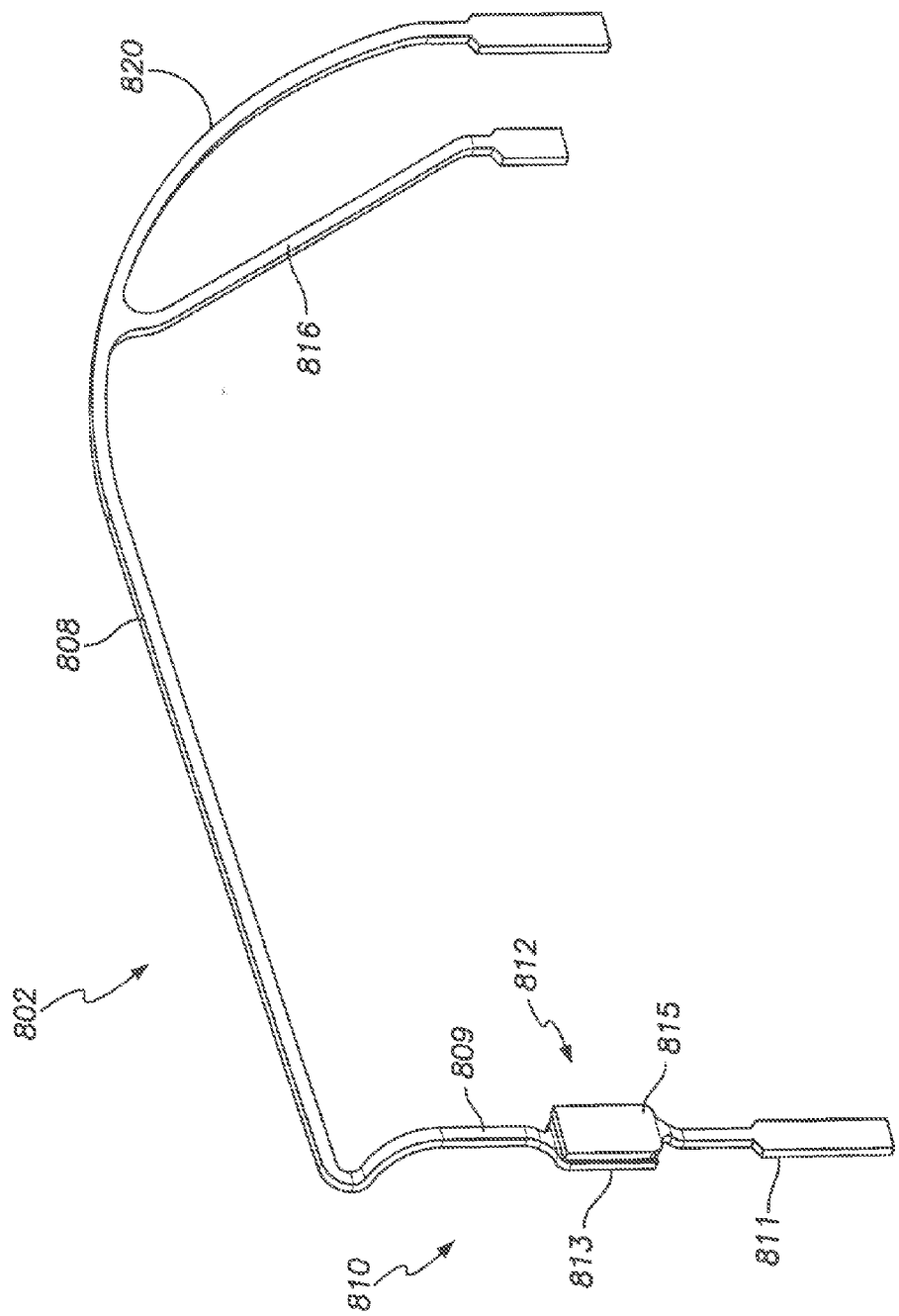
FIG. 16 provides another view of the antenna of FIG. 12 (without the header or other header components shown in this figure)
Figure 17:
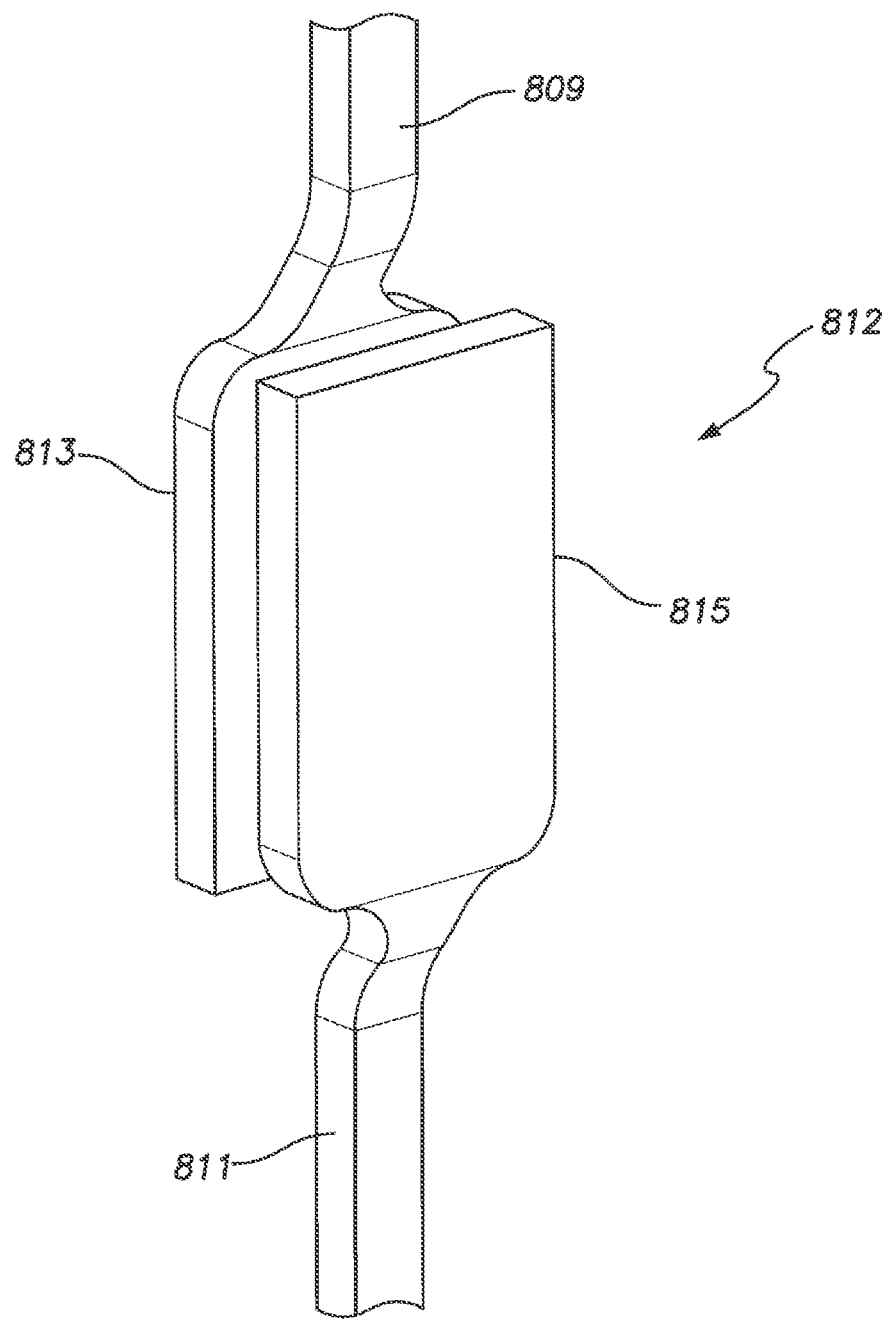
FIG. 17 provides a close-up view of the parallel capacitor plates of the antenna of FIG. 16 (again without any non-conductive material shown between the capacitor plates)

FIGS. 13-17 illustrate other views of the inverted E antenna. Briefly, FIG. 13 shows an end view that more clearly illustrates the relative spacing of the capacitor plates. This figure also identifies a couple of the other bores (856 and 858) formed along a side portion of the header for insertion of sensing/pacing lead ring connectors into the aforementioned header ring connector components. FIG. 14 shows another end view that also illustrates the spacing of the capacitor plates. FIG. 15 shows an angled end view of the header. FIG. 16 shows just the inverted E antenna 802, without header or CRMD to more clearly show configuration of its various components. FIG. 17 shows just parallel plates of the capacitor. As shown, the bottom end of antenna portion 809 and the top end of antenna portion 811 each flare outwardly by an amount sufficient to leave space between plates 813 and 815 to accommodate the non-conductive material (not shown.) During device design, the distance between the plates is set in conjunction with the thickness and characterizes of the non-conductive material to provide a desired amount of capacitance (to within a specified tolerance.)

Figure 18:
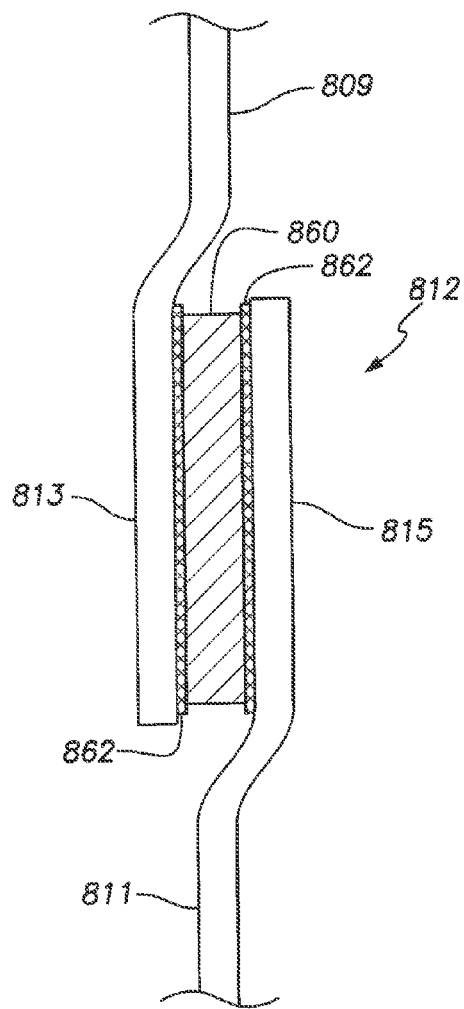
FIG. 18 provides a side view of the capacitor plates of the antenna of FIG. 17 with a non-conducting ceramic plate mounted therebetween using epoxy.
Figure 19:
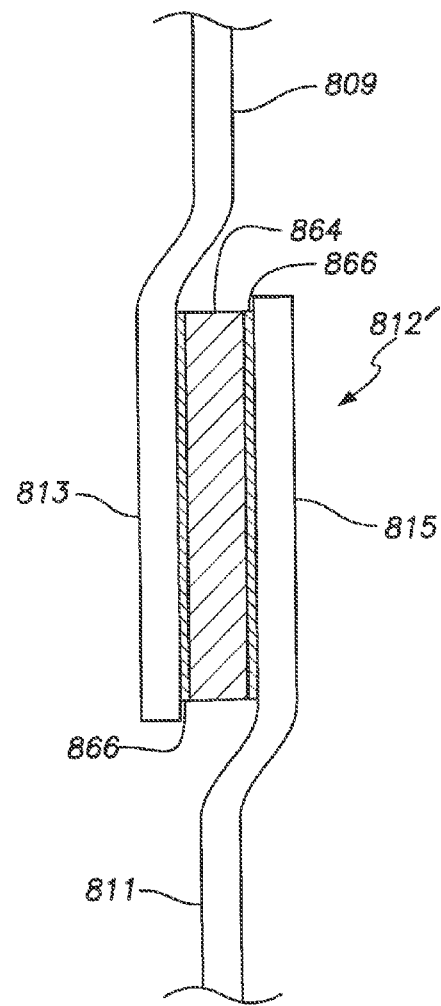
FIG. 19 provides a side view of the capacitor plates of the antenna of FIG. 17 with titanium sputtered onto both sides of the ceramic plate, which is welded between the parallel plates.

FIGS. 18 and 19 illustrate the capacitor with non-conductive material. Briefly, FIG. 18 shows an example of capacitor 812 where one or more ceramic dielectric plates 860 are interposed or "sandwiched" between the parallel plates 813 and 815 and bonded to the plates by an implantable grade epoxy 862 (or other suitable material.) FIG. 19 shows an alternative capacitor 812' where titanium 866 (or another suitable metal) is sputtered onto both side of a ceramic dielectric 864 plate of known thickness, which is cut to size and then welded between parallel plates 813 and 815 (or otherwise welded to the ends of ribbons 809 and 811.)

The antenna designs of FIGS. 12-19 offer some or all of the following advantages over the predecessor inverted E antenna design described above such as the embodiment where the capacitor is formed at the end of one of the antenna arms in conjunction with an adjacent portion of the device housing. (See, e.g., FIG. 7.) First, the spacing between the parallel plates of the new antenna can be more tightly controlled than with the predecessor design, which can improve antenna performance by decreasing variability of the capacitance. The new antenna preferably comes pre-assembled, so spacing can be measured and verified prior to assembly, which is not typically feasible with the predecessor antenna design. Secondly, the new antenna can use a ceramic as the dielectric between the two plates, which will not likely saturate with body fluid over time and will maintain a substantially constant thickness throughout the lifetime of the device while implanted, which can improve overall antenna performance. Since ceramics also have a generally higher dielectric constant than epoxies, this also allows for a smaller plate size to achieve the same capacitance. Thirdly, since the new design does not require a large plate at the end of the antenna arm to create the capacitance, the area of the housing that would otherwise be occupied by the plate can be utilized for other purposes, such as anchoring, moving a lower bore closer to the device housing, etc. By moving the bore down, the size of the headers can be reduced to improve marketability and competitiveness.

In addition, the new design can increase the RF performance of the header by reducing the effect of leads. (The predecessor design has some degree of antenna variation once the leads are connected to the bores of the headers.) Moreover, because the capacitor is mounted more in the direction of the radiation and not in the direction of the device can, it helps improve radiation efficiency. Yet another possible benefit is that the new design does not rely on the surrounding metallic components to achieve the desired capacitance value in the same way that the predecessor inverted E antenna does. As such, the design can change more easily during the development process. With the predecessor design, any change to metallic component positioning within the header would typically require extensive retesting and simulation efforts to verify that the performance was still adequate. Since ICDs have generally tighter RF performance requirements than pacers, the predecessor design might not readily allow engineers to achieve the desired performance for use with low cost ICDs.

Inverted E Antenna with Stacked Plates Formed Along Capacitive Branch

Figure 20:
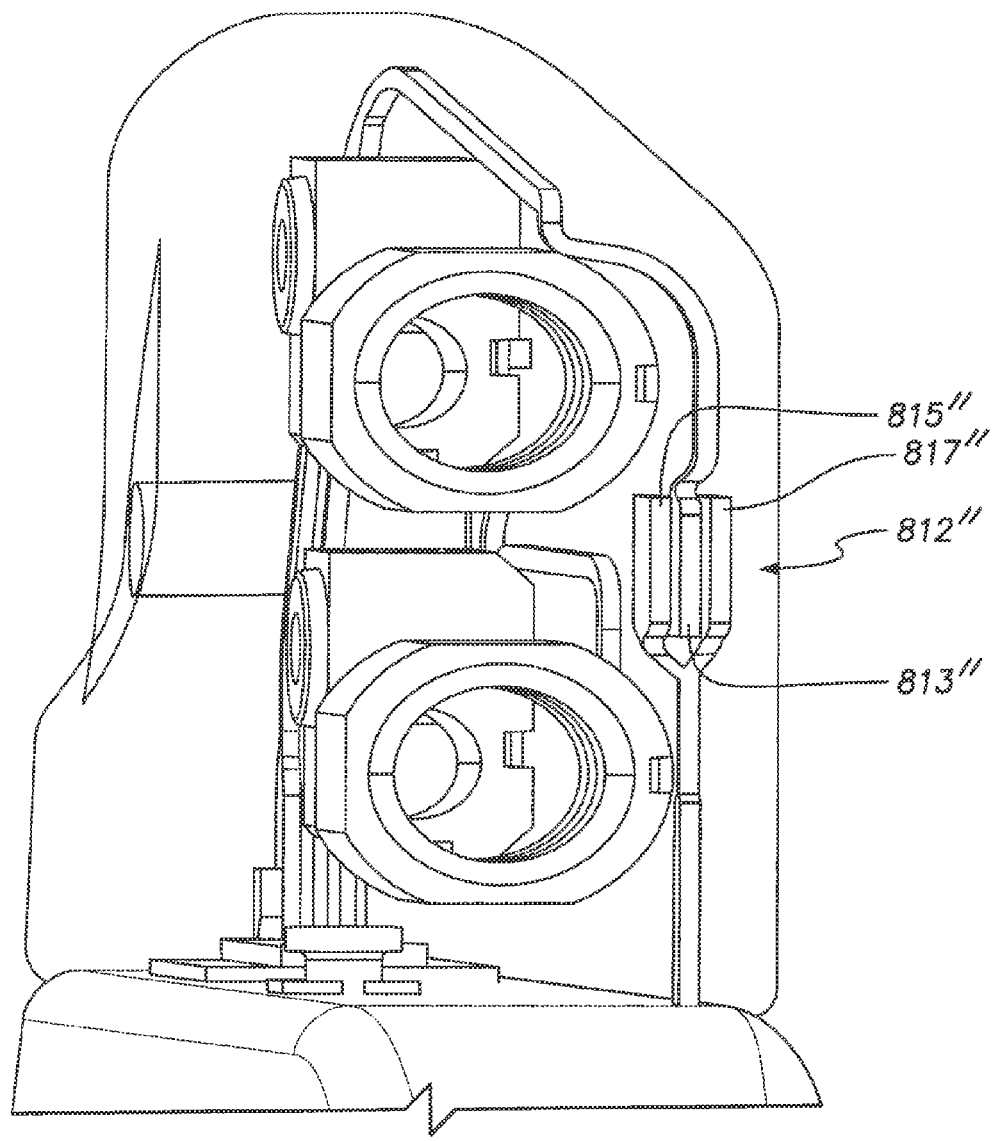
FIG. 20 illustrates yet another embodiment of the inverted E antenna of FIG. 3, wherein a stacked capacitor is employed.
Figure 21:
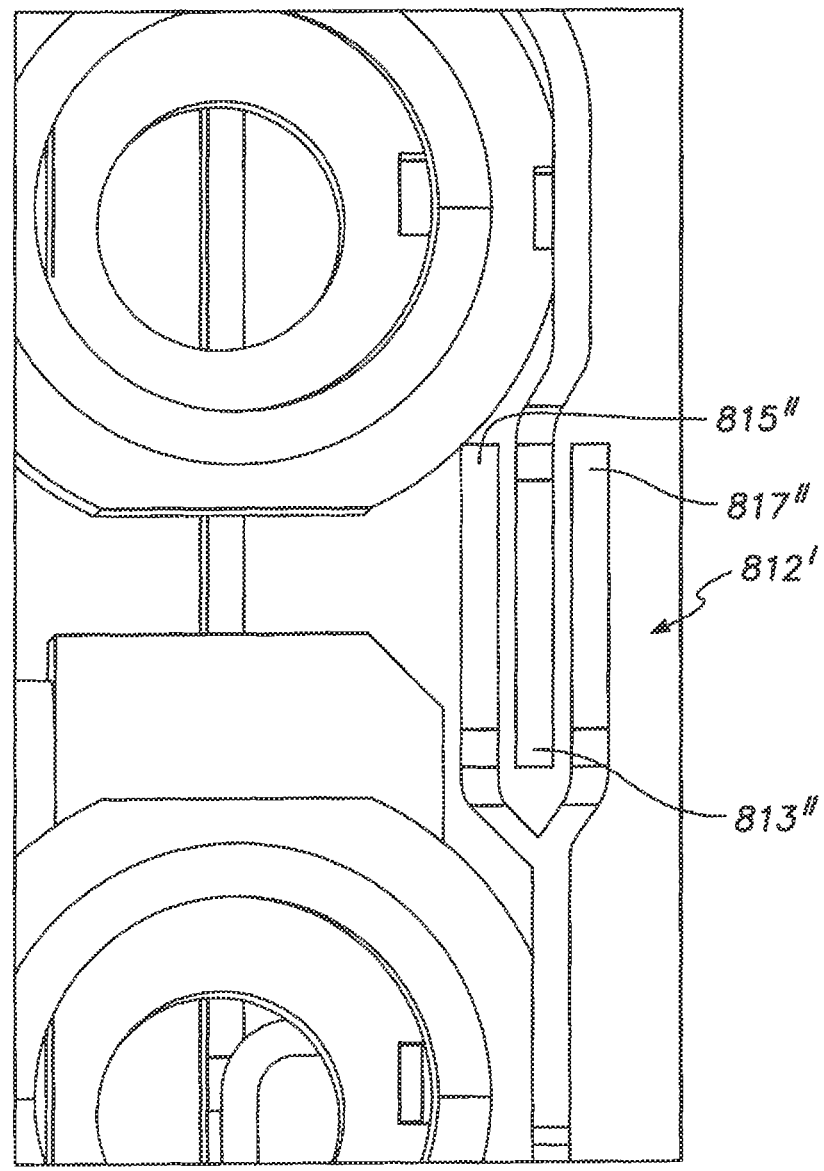
FIG. 21 provides a side view of the capacitor plates of the antenna of FIG. 20, wherein a stacked capacitor is employed.
Figure 22:
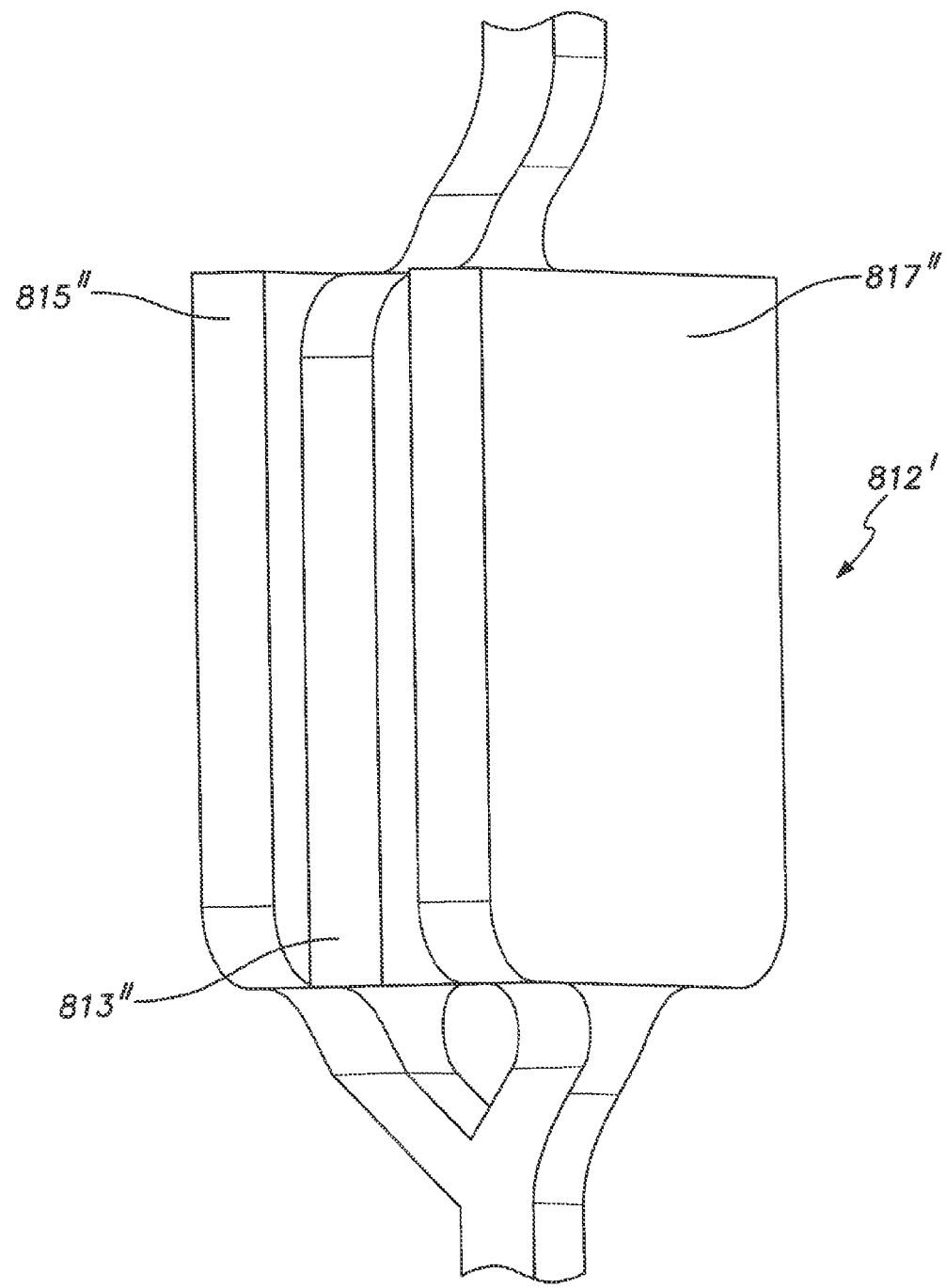
FIG. 22 provides a close-up view of the capacitor plates of the antenna of FIG. 20, wherein a stacked capacitor is employed.

FIGS. 20-22 illustrate yet another embodiment of inverted E antenna, which includes a stacked plate capacitor formed along the capacitive branch. Since the overall antenna has already been described, only the stacked capacitor will be specifically discussed in this section. (Note that only the components of the stacked capacitor are specifically denoted with reference numerals in these figures. The other components shown in the figures are denoted by reference numerals in the figures described above. Note also that in these particular figures, the dielectric material to be employed between the plates is not shown so that the configuration of the plates can be more clearly seen. See FIGS. 18 and 19 for illustrations of ceramic materials that can be employed as dielectrics within the capacitor.) Referring first to FIG. 20, stacked capacitor 812" includes a central descending plate 813", which is sandwiched between two ascending plates 815" and 817". FIGS. 21 and 22 show the stacked capacitor in close-up views. In this regard, by forming a capacitor within the arms of the antenna, such a configuration lends itself well to having multiple plates stacked in parallel. One benefit is that for headers requiring large capacitor plates (relative to the header size), the plate size may be limited by the ring blocks, bore holes, etc (see FIG. 12.) With multiple plates stacked in parallel, engineers can take advantage of the space between the bore holes (see FIG. 13) to double or triple the capacitance.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method of fabrication of an implantable medical device for implant within a patient, the method comprising:
   providing a case, wherein the case is adapted to contain pulse generating circuitry and radio frequency (RF) communication components;
   providing feedthrough components to electrically connect the pulse generating circuitry and the radio components to components exterior to the case;
   connecting connector components to respective feedthrough components, wherein the connector components are arranged in one or more columns defining a first end adapted for receiving one or more implantable leads and a second opposing end;
   fitting an inverted E-antenna over the connector components, wherein (i) the inverted E-antenna comprises a first branch including a capacitor, a second branch to provide an RF signal feed, a third branch to provide a shunt to ground, and an main arm connecting the first, second, and third branches, (ii) the fitting causes the inverted E-antenna to span at least a distance from the first end to the second opposing end defined by the connector components, and (iii) the first branch of the inverted E-antenna comprises a curved portion to dispose the capacitor of the third component to a side of one or more connector components at the first end adapted for receiving one or more implantable leads; and
   providing a header over the inverted E-antenna and the connector components, wherein the inverted E-antenna is disposed adjacent to an outer edge of the header.

2. The method of claim 1 wherein the first branch comprises a first ribbon segment and a second ribbon segment, wherein the first ribbon segment is connected to the main arm.

3. The method of claim 2 further comprising:
connecting the second ribbon segment to the case.

4. The method of claim 2 wherein the first ribbon segment comprises a first plate component and the second ribbon segment comprises a second plate component.

5. The method of claim 4 wherein the first and second plates are mechanically attached to each other with dielectric material disposed between the first and second plates to form the capacitor.

6. The method of claim 5 wherein the dielectric material is a ceramic plate.

7. The method of claim 2 wherein the second ribbon segment comprises first and second plate components and the first ribbon segment component comprises a third plate component disposed between the first and second plates to form the capacitor.

8. The method of claim 1 wherein a major surface of the case defines a first plane and the capacitor of the first branch defines a second plane that is in a parallel plane relationship with the first plane.

9. The method of claim 1 wherein the providing a header comprises providing a precast header structure.

10. The method of claim 1 wherein the providing a header comprises providing epoxy material to form the header.

11. The method of claim 1 further comprising:
connecting the second branch to the case at a first location adjacent to the second opposing end defined by the connector components; and connecting the first branch to the case at a second location adjacent to the first end defined by the connector components, wherein the second branch is connected on a side of the connector components that is opposite to a side of the connector components where the capacitor of the first branch is located.

12. The method of claim 1 wherein the implantable medical device is a cardiac rhythm management device.

13. The method of claim 1 wherein the RF components include one or more of Medical implant Communication Service (MICS) components and Medical Device Radiocommunications Service (MedRadio) components.

* * * * *